United States Patent
Stibich et al.

(10) Patent No.: US 9,867,894 B2
(45) Date of Patent: Jan. 16, 2018

(54) GERMICIDAL APPARATUSES WITH CONFIGURATIONS TO SELECTIVELY CONDUCT DIFFERENT DISINFECTION MODES INTERIOR AND EXTERIOR TO THE APPARATUS

(71) Applicant: Xenex Disinfection Services, LLC., San Antonio, TX (US)

(72) Inventors: Mark A. Stibich, Houston, TX (US); Paul P. Froutan, Katy, TX (US); Sarah E. Simmons, San Antonio, TX (US); Charles Dale, San Antonio, TX (US)

(73) Assignee: Xenex Disinfection Services, LLc., San Antonio, TX (US)

( * ) Notice: Subject to any disclaimer, the term of this patent is extended or adjusted under 35 U.S.C. 154(b) by 0 days.

(21) Appl. No.: 14/790,827

(22) Filed: Jul. 2, 2015

(65) Prior Publication Data
US 2017/0000916 A1 Jan. 5, 2017

(51) Int. Cl.
*A61L 2/24* (2006.01)
*A61L 2/14* (2006.01)
(Continued)

(52) U.S. Cl.
CPC .................................. *A61L 2/24* (2013.01); *A61L 2/08* (2013.01); *A61L 2/14* (2013.01); *A61L 2/18* (2013.01);
(Continued)

(58) Field of Classification Search
CPC ..... A61L 2/08; A61L 2/10; A61L 2/14; A61L 2/16; A61L 2/18; A61L 2/20; A61L 2/22;
(Continued)

(56) References Cited

U.S. PATENT DOCUMENTS

| 2,182,732 A | 12/1939 | Meyer et al. |
| 2,215,635 A | 9/1940 | Collins |

(Continued)

FOREIGN PATENT DOCUMENTS

| CA | 2569130 | 6/2008 |
| CN | 87203475 | 8/1988 |

(Continued)

OTHER PUBLICATIONS

Kowalski et al., "Mathematical Modeling of Ultraviolet Germicidal Irradiation for Air Disinfection," Quantitative Microbiology 2, 2000, pp. 249-270.

(Continued)

*Primary Examiner* — Timothy Cleveland
(74) *Attorney, Agent, or Firm* — Egan Peterman Enders Huston

(57) ABSTRACT

Apparatuses are provided which include one or more germicidal sources, power circuitry coupled to the germicidal source/s, and a shield. The shield and/or at least one of the germicidal source/s are moveable within the apparatus and the apparatus is configured such that the shield and/or the germicidal source/s may be brought in and out of proximity with the other and upon doing so germicide projected from one or more of the germicidal source/s is either substantially contained in the apparatus or is projected exterior to the apparatus for different disinfection modes of the apparatus. The apparatuses include a processor and processor-executable program instructions for activating the power circuitry to operate the at least one germicidal source when the germicidal source is not encased within the apparatus and for activating the power circuitry to operate at least one germicidal source when the germicidal source/s are encased within the apparatus.

34 Claims, 8 Drawing Sheets

(51) Int. Cl.

| | | |
|---|---|---|
| *A61L 2/08* | (2006.01) | |
| *A61L 2/18* | (2006.01) | |
| *A61L 2/20* | (2006.01) | |
| *A61L 9/18* | (2006.01) | |
| *A61L 9/22* | (2006.01) | |
| *A61L 9/015* | (2006.01) | |

(52) U.S. Cl.
CPC ............... *A61L 2/20* (2013.01); *A61L 9/015* (2013.01); *A61L 9/18* (2013.01); *A61L 9/22* (2013.01)

(58) Field of Classification Search
CPC ... A61L 2/24; A61L 9/015; A61L 9/14; A61L 9/16; A61L 9/18; A61L 9/20; A61L 9/22
See application file for complete search history.

(56) References Cited

U.S. PATENT DOCUMENTS

| | | | |
|---|---|---|---|
| 2,382,939 | A | 8/1945 | Koch |
| 2,392,095 | A | 1/1946 | Lemmers |
| 2,615,120 | A | 10/1952 | Macksoud |
| 3,418,069 | A | 12/1968 | Eugene et al. |
| 4,005,135 | A | 1/1977 | Helding |
| 4,229,658 | A | 10/1980 | Gonser |
| 4,877,964 | A | 10/1989 | Tanaka et al. |
| 4,896,042 | A | 1/1990 | Humphreys |
| 5,023,460 | A | 6/1991 | Foster, Jr. et al. |
| 5,144,146 | A | 9/1992 | Wekhof |
| 5,220,734 | A | 6/1993 | Carver |
| 5,221,139 | A | 6/1993 | Belfer |
| 5,344,433 | A | 9/1994 | Talmore |
| 5,373,430 | A | 12/1994 | McDermott |
| 5,744,094 | A | 4/1998 | Castberg et al. |
| 5,768,853 | A | 6/1998 | Bushnell et al. |
| 5,891,399 | A | 4/1999 | Owesen |
| 5,925,885 | A | 7/1999 | Clark et al. |
| 6,203,060 | B1 | 3/2001 | Cech et al. |
| 6,242,753 | B1 | 6/2001 | Sakurai |
| 6,264,836 | B1 | 7/2001 | Lantis |
| 6,398,970 | B1 | 6/2002 | Justel et al. |
| 6,403,030 | B1 | 6/2002 | Horton, III |
| 6,447,720 | B1 | 9/2002 | Horton, III et al. |
| 6,465,799 | B1 | 10/2002 | Kimble et al. |
| 6,493,087 | B1 | 12/2002 | Fabinski et al. |
| 6,539,727 | B1 | 4/2003 | Burnett |
| 6,566,659 | B1 | 5/2003 | Clark et al. |
| 6,656,424 | B1 | 12/2003 | Deal |
| 6,759,664 | B2 | 7/2004 | Thompson et al. |
| 6,774,382 | B2 | 8/2004 | Toshida |
| 6,897,460 | B2 | 5/2005 | Kobayashi et al. |
| 6,911,177 | B2 | 6/2005 | Deal |
| 6,932,494 | B1 | 8/2005 | Burnett et al. |
| 6,932,903 | B2 | 8/2005 | Chang |
| 6,962,239 | B2 | 11/2005 | Shikai et al. |
| 7,122,115 | B2 | 10/2006 | Holt et al. |
| 7,153,808 | B2 | 12/2006 | Iwamoto et al. |
| 7,175,806 | B2 | 2/2007 | Deal et al. |
| 7,329,026 | B1 | 2/2008 | Hayman et al. |
| 7,371,351 | B2 | 5/2008 | Goswami |
| 7,380,627 | B2 | 6/2008 | Huang et al. |
| 7,423,367 | B2 | 9/2008 | Lantis et al. |
| 7,459,694 | B2 | 12/2008 | Scheir et al. |
| 7,476,006 | B2 | 1/2009 | Hinds |
| 7,498,004 | B2 | 3/2009 | Saccomanno |
| 7,829,867 | B2 | 11/2010 | Hlavinka et al. |
| 8,038,949 | B2 | 10/2011 | Horne et al. |
| 8,142,713 | B2 | 3/2012 | Gordon |
| 8,193,515 | B2 | 6/2012 | Kreitenberg |
| 8,203,126 | B2 | 6/2012 | Rocha-Alvarez et al. |
| 8,236,236 | B2 | 8/2012 | Garner |
| 8,354,057 | B2 | 1/2013 | Heselton et al. |
| 8,481,985 | B2 | 7/2013 | Neister |
| 8,791,441 | B1 | 7/2014 | Lichtblau |

| | | | |
|---|---|---|---|
| 2003/0085631 | A1 | 5/2003 | Cech et al. |
| 2003/0086821 | A1 | 5/2003 | Matthews |
| 2003/0137834 | A1 | 7/2003 | Jigamian et al. |
| 2003/0170152 | A1 | 9/2003 | Kobayashi et al. |
| 2004/0024278 | A1 | 2/2004 | Megerle |
| 2004/0052702 | A1 | 3/2004 | Shuman et al. |
| 2004/0140782 | A1 | 7/2004 | Okabe et al. |
| 2004/0175290 | A1 | 9/2004 | Scheir et al. |
| 2004/0202570 | A1 | 10/2004 | Nadkarni |
| 2004/0244138 | A1 | 12/2004 | Taylor et al. |
| 2005/0010331 | A1 | 1/2005 | Taylor et al. |
| 2005/0025662 | A1 | 2/2005 | Lestician |
| 2005/0058013 | A1 | 3/2005 | Warf et al. |
| 2005/0133740 | A1 | 6/2005 | Gardner |
| 2005/0151937 | A1 | 7/2005 | Sugitani |
| 2005/0171636 | A1 | 8/2005 | Tani |
| 2005/0186108 | A1 | 8/2005 | Fields |
| 2006/0045817 | A1 | 3/2006 | Home et al. |
| 2006/0244403 | A1 | 11/2006 | Christensson et al. |
| 2006/0261291 | A1 | 11/2006 | Gardner |
| 2006/0284109 | A1 | 12/2006 | Scheir et al. |
| 2007/0140893 | A1 | 6/2007 | McVey et al. |
| 2007/0188113 | A1 | 8/2007 | Okamoto |
| 2007/0231189 | A1 | 10/2007 | Jung et al. |
| 2007/0231204 | A1 | 10/2007 | Hyde et al. |
| 2007/0253860 | A1 | 11/2007 | Schroder |
| 2008/0056933 | A1 | 3/2008 | Moore et al. |
| 2008/0112845 | A1 | 5/2008 | Dunn et al. |
| 2008/0213128 | A1 | 9/2008 | Rudy et al. |
| 2008/0253941 | A1 | 10/2008 | Wichers et al. |
| 2008/0260601 | A1 | 10/2008 | Lyon |
| 2009/0123343 | A1 | 5/2009 | Kwiatkowski |
| 2009/0129974 | A1 | 5/2009 | McEllen |
| 2009/0191100 | A1 | 7/2009 | Deal |
| 2009/0217547 | A1 | 9/2009 | Kim et al. |
| 2009/0314308 | A1 | 12/2009 | Kim et al. |
| 2009/0323181 | A1 | 12/2009 | Andrews et al. |
| 2010/0026726 | A1 | 2/2010 | Fujii et al. |
| 2010/0044319 | A1 | 2/2010 | Engel et al. |
| 2010/0078574 | A1 | 4/2010 | Cooper et al. |
| 2010/0082193 | A1 | 4/2010 | Chiappetta |
| 2010/0183476 | A1 | 7/2010 | Lu |
| 2011/0002821 | A1 | 1/2011 | Hyde et al. |
| 2011/0054574 | A1 | 3/2011 | Felix |
| 2011/0206554 | A1 | 8/2011 | Anderle et al. |
| 2011/0215261 | A1 | 9/2011 | Lyslo et al. |
| 2012/0047763 | A1 | 3/2012 | Abramovich et al. |
| 2012/0056102 | A1 | 3/2012 | Stanley et al. |
| 2012/0093688 | A1 | 4/2012 | Harmon et al. |
| 2012/0119108 | A1 | 5/2012 | Goldshtein et al. |
| 2012/0126134 | A1 | 5/2012 | Deal et al. |
| 2012/0023216 | A1 | 9/2012 | Flaherty et al. |
| 2012/0313014 | A1* | 12/2012 | Stibich .............. A61L 2/10 250/492.1 |
| 2012/0313532 | A1 | 12/2012 | Stibich et al. |
| 2012/0315186 | A1 | 12/2012 | Davis |
| 2013/0002445 | A1 | 1/2013 | Stibich et al. |
| 2013/0224086 | A1 | 8/2013 | Stibich et al. |
| 2013/0330235 | A1 | 12/2013 | Stibich et al. |
| 2014/0060095 | A1 | 3/2014 | Shur et al. |
| 2014/0061509 | A1 | 3/2014 | Shur et al. |
| 2014/0158917 | A1 | 6/2014 | Stibich et al. |
| 2014/0348701 | A1 | 11/2014 | Kirschman |
| 2015/0190540 | A1 | 7/2015 | Stibich et al. |
| 2015/0320897 | A1 | 11/2015 | Stibich et al. |

FOREIGN PATENT DOCUMENTS

| | | |
|---|---|---|
| CN | 2117167 | 9/1992 |
| CN | 2540625 | 3/2003 |
| CN | 2678651 | 2/2005 |
| CN | 2700714 | 5/2005 |
| CN | 1715793 | 1/2006 |
| CN | 101633525 | 1/2010 |
| CN | 201439877 | 4/2010 |
| CN | 201510540 | 6/2010 |
| CN | 101890174 | 11/2010 |
| CN | 201755324 | 3/2011 |
| DE | 149020 | 6/1981 |

(56) References Cited

FOREIGN PATENT DOCUMENTS

| | | |
|---|---|---|
| EP | 0566238 | 10/1993 |
| EP | 2172097 | 4/2010 |
| EP | 2174670 | 4/2010 |
| EP | 2314802 | 4/2011 |
| GB | 2203283 | 10/1988 |
| GB | 2452341 | 3/2009 |
| JP | 57-164062 | 10/1982 |
| JP | S61-158455 | 7/1986 |
| JP | H01-221166 | 9/1989 |
| JP | H05-182635 | 7/1993 |
| JP | H05284905 A | 11/1993 |
| JP | 06-063107 | 3/1994 |
| JP | H06-142175 | 5/1994 |
| JP | H07-289616 | 11/1995 |
| JP | H08-196606 | 8/1996 |
| JP | H09-161723 | 6/1997 |
| JP | H10-246468 | 9/1998 |
| JP | H11-104224 | 4/1999 |
| JP | H11-216336 | 8/1999 |
| JP | 2001-340439 | 12/2001 |
| JP | 2002-000713 | 1/2002 |
| JP | 2002-191685 | 7/2002 |
| JP | 2002-224210 | 8/2002 |
| JP | 2003-135581 | 5/2003 |
| JP | 2003-262369 | 9/2003 |
| JP | 2004-073775 | 3/2004 |
| JP | 2006314661 A | 11/2006 |
| JP | 2010-276737 | 12/2010 |
| JP | 2011-252612 | 12/2011 |
| KR | 10-2006-0097854 | 9/2006 |
| KR | 2006-0102300 | 9/2006 |
| KR | 20-2011-003951 | 4/2011 |
| WO | 93/23730 | 11/1993 |
| WO | 94/06482 | 3/1994 |
| WO | 01/60419 | 8/2001 |
| WO | 02/058744 | 8/2002 |
| WO | 2005/082426 | 9/2005 |
| WO | 2006/070281 | 7/2006 |
| WO | 2007/001364 | 1/2007 |
| WO | 2007/008879 | 1/2007 |
| WO | 2007/020282 | 2/2007 |
| WO | 2007/081401 | 7/2007 |
| WO | 2007/089312 | 8/2007 |
| WO | 2008/144202 | 11/2008 |
| WO | 2011/088394 | 7/2011 |
| WO | 2012085250 A1 | 6/2012 |
| WO | 2012/142427 | 10/2012 |
| WO | 2014/022717 | 2/2014 |
| WO | 2014/060051 | 4/2014 |
| WO | 2014/088580 | 6/2014 |
| WO | 2014/100493 | 6/2014 |
| WO | 2015054389 | 4/2015 |
| WO | 2016044759 | 3/2016 |

OTHER PUBLICATIONS hgmmagzine.com; Solutions, Products & Services, On Our Radar, Dec. 2010, 3 pgs.

Xenex Disinfection Services, Search Report and Written Opinion, Filed Jun. 29, 2016, PCT/US2016/040150, dated Sep. 30, 2016, 13 pgs.

* cited by examiner

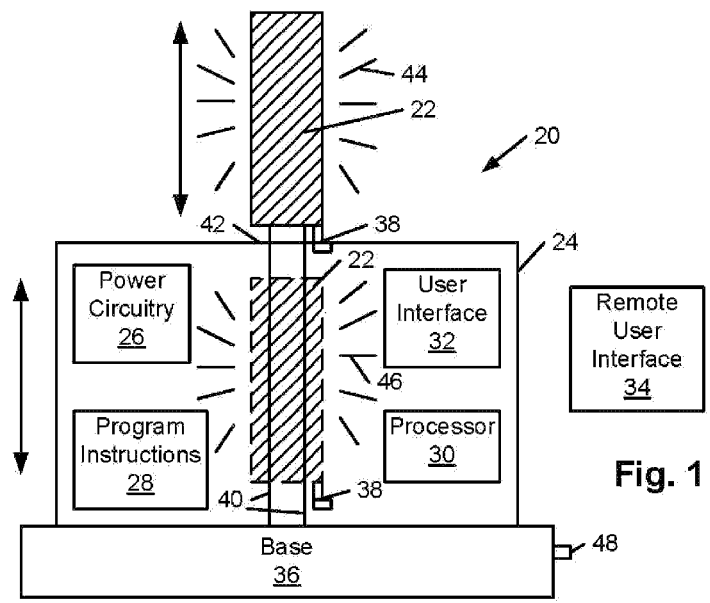
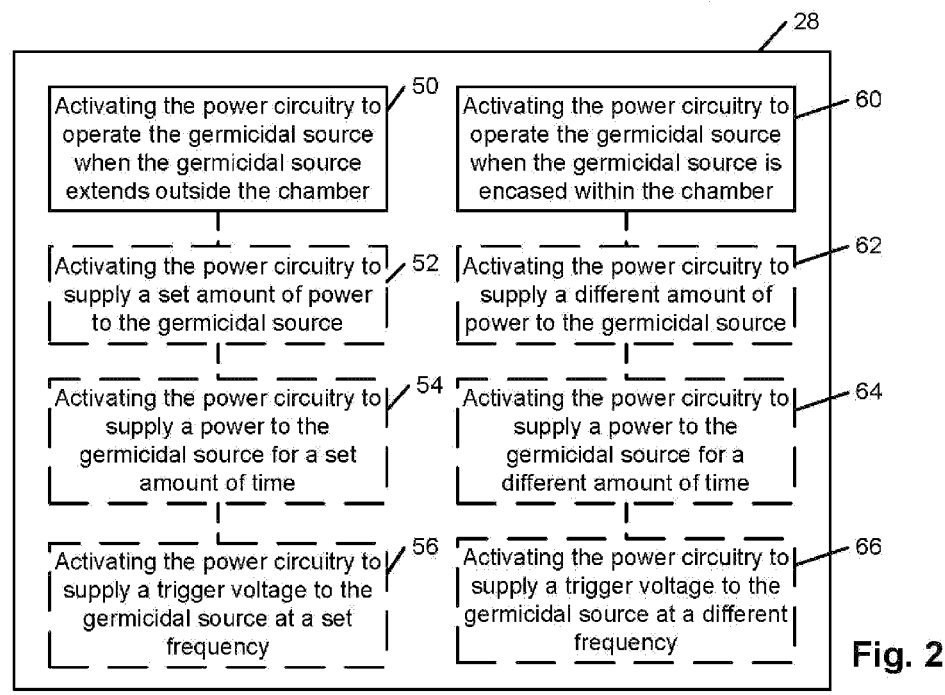

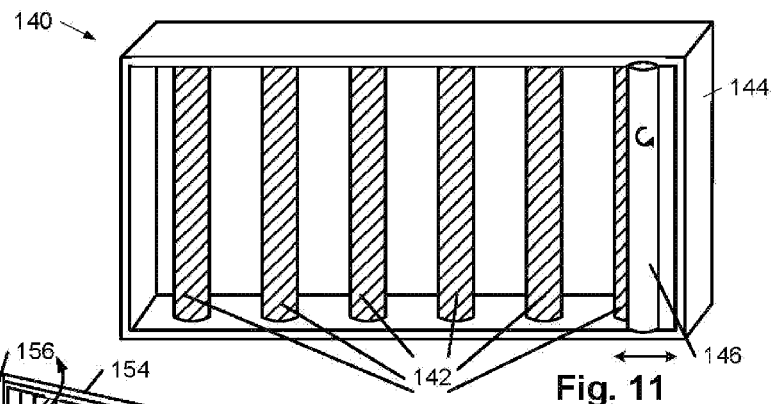
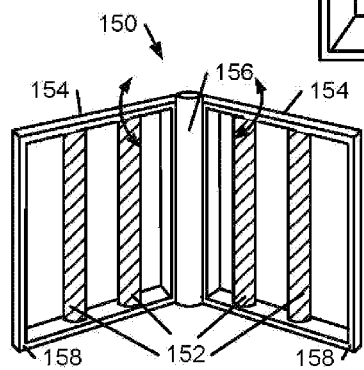
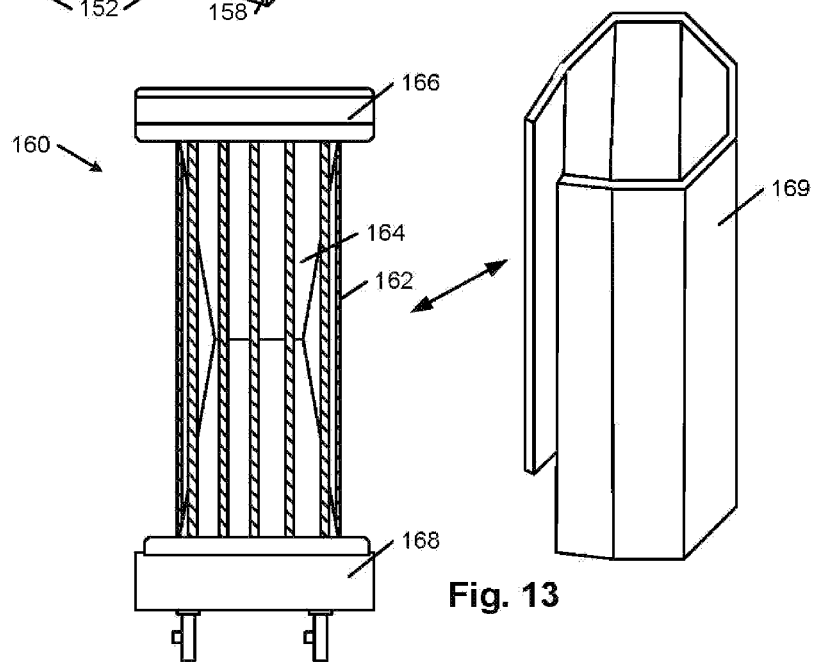

GERMICIDAL APPARATUSES WITH CONFIGURATIONS TO SELECTIVELY CONDUCT DIFFERENT DISINFECTION MODES INTERIOR AND EXTERIOR TO THE APPARATUS

BACKGROUND OF THE INVENTION

1. Field of the Invention

This invention generally relates to germicidal devices and, more specifically, to germicidal apparatuses with configurations for selectively conducting different disinfection modes interior and exterior to the apparatus.

2. Description of the Related Art

The following descriptions and examples are not admitted to be prior art by virtue of their inclusion within this section.

Disinfection of air and surfaces in rooms and areas is becoming increasingly important as pathogenic microorganisms have been shown to cause infections when present in occupied rooms or areas. This is especially important as antimicrobial resistant organisms are becoming more prevalent and increasingly difficult to treat. In general, the objective of a disinfection process in areas/rooms is to reduce the number of pathogenic microorganisms in the air and/or on surfaces in the area/room to a level which is much less harmful to human health. In order to limit or prevent exposure of germicides and/or distractions to occupants of a room or area, area/room disinfection is typically performed by trained cleaning personnel or by an automated device which disperses a germicide into an ambient of a room after the room has been vacated by the previous occupants. In order to maximize the number of surfaces treated but yet minimize the treatment time, the automated devices are generally configured to distribute a germicide in a spacious manner to an ambient of a room or area. For example, some automated area/room disinfection devices are configured to distribute a germicide 360 degrees around the device. In addition, many automated area/room disinfection devices are configured to distribute an effective amount of germicide to achieve between a 2-log and 4-log reduction in bacterial contamination on surfaces within a room or area that are greater than 1 meter or even 2 or 3 meters from the device. In any case, in addition to disinfecting surfaces in an area or room, the automated area/room disinfection devices innately disinfect some of the air in the area or room by the dispersion of the germicide from the device to the surfaces.

As noted above, automated area/room disinfection devices are often used in vacated areas/rooms in order to limit or prevent exposure of germicides to individuals. It is often desirable, however, to conduct disinfection processes in occupied rooms without exposing individuals to germicides. Examples of automated disinfection devices and systems which may be used in occupied areas and rooms are devices and systems which are configured to disinfect and circulate air through a room without exposing germicides exterior to the devices and systems. For instance, some HVAC systems have an ultraviolet light source within its interior to disinfect air before being introduced into a room. Furthermore, standalone air disinfection units for individual rooms are known. Moreover, standalone closed system devices exist for disinfecting small objects without exposing germicides exterior to the devices. In addition to inhibiting exposure of germicide to their exteriors, many air and object disinfection devices and systems are configured to optimize the efficiency at which the air/objects are treated, specifically limiting the distance at which a germicide travels to disinfect an air stream flowing therethrough or an object placed inside the device. Given such objectives are contrary to the objectives of most area/room disinfection devices as set forth above, all types of disinfection devices/systems (i.e., area/room disinfection devices, contained air disinfection devices or systems, and closed system object disinfection devices) are generally needed if surface and air disinfection processes are desired when areas or rooms are occupied as well as when the areas or rooms are unoccupied.

Accordingly, it would be beneficial to develop devices and/or systems that are usable for disinfection processes when areas or rooms are occupied and when the areas or rooms are unoccupied. It would be further beneficial to include configurations in such devices and/or systems which optimize the efficacies of the different disinfection modes.

SUMMARY OF THE INVENTION

The following description of various embodiments of apparatuses is not to be construed in any way as limiting the subject matter of the appended claims.

Embodiments of apparatuses include one or more germicidal sources, power supply circuitry coupled to the germicidal source/s, and a shield. The shield and/or at least one of the germicidal source/s are repositionable within the apparatus and the apparatus is configured such that the shield and/or the germicidal source/s may be brought in proximity with each other and upon doing so germicide projected from the germicidal source/s is substantially contained in the apparatus. In addition, the shield and/or at least one of the germicidal source/s are repositionable within the apparatus and the apparatus is configured such that the shield and/or the germicidal source/s may be brought out of proximity with each other and upon doing so germicide projected from at least one of the germicidal source/s is projected exterior to the apparatus. In accordance with such germicidal containment and dispersal options for the apparatuses, the apparatuses further include a processor and a storage medium having program instructions which are executable by the processor for activating the power supply circuitry to operate the at least one germicidal source when the germicidal source is not encased within the apparatus and for activating the power supply circuitry to operate at least one germicidal source when the germicidal source/s are encased within the apparatus.

In some apparatuses, the shield may be a chamber dimensionally configured to contain the germicidal source/s and/or the shield may be configured in accompaniment with other features of the apparatus to form a chamber sufficient to encase the germicidal source/s. In cases in which the shield is a chamber, the chamber may be arranged within the apparatus such that a port of the chamber which is dimensionally configured to receive at least one of the germicidal source/s is in linear alignment with the at least one germicidal source. In such embodiments, the at least one germicidal source and/or the chamber may be linearly displaceable within the apparatus such that the germicidal source/s may be contained within the chamber and the at least one germicidal source may be at least partially arranged exterior to the chamber for respectively different modes of operation for the apparatus.

Some embodiments of the apparatuses further include a sensor to detect whether the germicidal source/s and the shield are in proximity with each other and/or to detect whether the germicidal source/s and the shield are out of proximity with each other. Alternatively stated, the apparatuses may include a sensor to detect whether the germicidal source/s are encased in the apparatus and/or to detect whether the germicidal source/s are not encased in the apparatus. In some cases, the apparatuses may include an electronic user interface, a processor, and a storage medium having program instructions which are executable by the processor for receiving input from the electronic user interface to start operation of the apparatus and upon receiving the input, determining from the sensor whether the germicidal source/s are in or out of proximity with each or whether the germicidal source/s are encased in the apparatus or not encased in the apparatus. In some cases, the apparatuses may include program instructions for activating the power supply circuitry in accordance with different sets of operating parameters for the apparatus upon respectively determining the germicidal source/s are encased or are not encased within the apparatus. In apparatuses which include multiple germicidal sources, the apparatuses may additionally or alternatively include program instructions for activating the power supply circuitry to selectively operate different subsets of the multiple germicidal sources upon respectively determining the germicidal sources are encased or are not encased within the apparatus.

Some embodiments of the apparatuses may include an electronic user interface having input controls allowing selection of different disinfection modes conducted by the apparatuses, including a first disinfection mode for primarily disinfecting a medium inside the apparatuses and a second disinfection mode for primarily disinfecting a medium exterior to the apparatuses. In such cases, the apparatuses further include program instructions for receiving input from the electronic user interface regarding a selected disinfection mode and for determining whether the shield and the germicidal source are in or out of proximity with each other. Further to such embodiments, the apparatus may include program instructions for activating a corrective action for the germicidal source/s and/or the shield to be repositioned in proximity with the other upon receiving input of the first disinfection mode and determining the shield and the germicidal source/s are out of proximity with each other. In addition, the apparatus may include program instructions for activating a corrective action for the germicidal source/s and/or the shield to be repositioned out of proximity with the other upon receiving input of the second disinfection mode and determining the shield and the germicidal source/s are in proximity with each other.

In some cases, the apparatuses may include program instructions for activating the power supply circuitry in accordance with a predetermined first set of operating parameters for the apparatus upon receiving input of the first disinfection mode and determining the shield and the germicidal source/s are in proximity with each other. Moreover, the apparatuses may include program instructions for activating the power supply circuitry in accordance with a predetermined second set of operating parameters for the apparatus different from the first set of operating parameters upon receiving input of the second disinfection mode and determining the shield and the germicidal source/s are out of proximity with each other. In apparatuses which include multiple germicidal sources, the apparatuses may include program instructions for additionally or alternatively activating the power supply circuitry to selectively operate a first subset of a plurality of germicidal sources upon receiving input of the first disinfection mode and determining the shield and the germicidal sources are in proximity with each other. In addition in such apparatuses, the apparatuses may include program instructions for activating the power supply circuitry to selectively operate a second subset of the multiple germicidal lamps different from the first subset of multiple germicidal lamps upon receiving input of the second disinfection mode and determining the shield and the germicidal sources are out of proximity with each other.

BRIEF DESCRIPTION OF THE DRAWINGS

Other objects and advantages of the invention will become apparent upon reading the following detailed description and upon reference to the accompanying drawings in which:

FIG. 1 illustrates an example of a disinfection apparatus having configurations to selectively perform a disinfection process interior to the apparatus and a disinfection process exterior to the apparatus;

FIG. 2 illustrates example program instructions for activating power circuitry of the apparatuses described herein to operate one or more germicidal sources of the apparatuses;

FIGS. 11-13 illustrate example configurations of other apparatuses having configurations to selectively perform a disinfection process interior to the apparatus and a disinfection process exterior to the apparatus.

Figure 3:
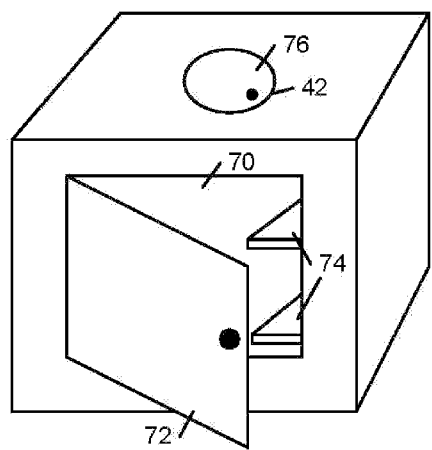
FIG. 3 illustrates a perspective view of an example chamber for the apparatus depicted in FIG. 1.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning to the drawings, examples of apparatuses used for disinfecting surfaces, objects and/or air interior to the apparatuses and exterior to the apparatuses are provided. In particular, FIGS. 1 and 11-13 depict examples of different apparatuses with configurations for enabling such interior and exterior disinfection capability. In addition, FIGS. 3-5 and 8-10 illustrate examples of different components which may comprise the apparatuses and specifically enable such selectivity. As shown in the drawings, the apparatuses may include processor-executable program instructions for automated operations of the apparatuses. FIGS. 2, 6, 7, and 14-17 depict flow charts of example processes which may be automated via such program instructions. As will be set forth in more detail below, the apparatuses and components described herein are not limited to the depictions in the drawings. Several other configurations of apparatuses and components may be considered. Furthermore, it is noted that the drawings are not necessarily drawn to scale.

Each of the apparatuses described herein includes a germicidal source. The germicidal source may be any device configured to generate a dispersible germicide. In particular, the germicidal source may be any device or apparatus configured to generate a germicide in form of a liquid, a vapor, a gas, a plasma or germicidal light. In some cases, a germicidal source may be configured to generate more than one type of germicide. As used herein, the term "germicide" refers to an agent for deactivating or killing microorganisms, particularly disease carrying and/or disease producing microorganisms (a.k.a, germs). The term "kill," as used herein, means to cause the death of an organism. In contrast, the term "deactivate," as used herein, means to render an organism unable to reproduce without killing. As such, a germicide which is configured to deactivate a microorganism, as used herein, refers to an agent which renders a microorganism unable to reproduce but leaves the organism alive. Furthermore, the term "germicidal source" as used herein refers to a collection of one or more components used to generate and disperse a germicide. In some embodiments, a germicidal source may include components in addition to the component/s used to generate the germicide to effect the dispersal of the germicide from the generation component/s. In any case, the apparatus described herein may include any number of germicidal sources, depending on the design specifications of the apparatus.

In some cases, a germicidal source of the apparatuses described herein may be configured to generate a liquid, vapor, gaseous or plasma germicide that is molecularly configured to deactivate and/or kill microorganisms. As used herein, the phrase "molecularly configured" refers to the elemental composition of a substance (i.e., the number and type of atoms making up a substance) to impart the function stated after the phrase. In some embodiments, the functionality of a liquid, vapor, gaseous or plasma germicide to deactivate and/or kill a microorganism may be attributed to the elements constituting the germicide and, thus, such germicides may be referenced as being molecularly configured to deactivate and/or kill microorganisms. This is in contrast to liquid, vapor, gaseous or plasma germicides which impart their deactivation and/or killing functionality by the manner in which they are used. For example, boiling water and steam are often effective sterilizing agents due to the temperature at which they are employed rather than their molecular composition. An example of a gaseous germicide which deactivates or kills microorganisms by the manner in which it is used is air at a very high temperature. Furthermore, the germicidal effectiveness of some plasma germicides is primarily due to the presence and activity of charged particles making up the plasma rather than the molecular composition of the charged particles.

An example of a gaseous germicide that is molecularly configured to kill microorganisms is ozone. Examples of plasmas germicides that are molecularly configured to deactivate or kill microorganisms are those that employ or generate reactive oxygen species. Examples of liquid and vapor germicides that are molecularly configured to deactivate or kill microorganisms include liquid and vapor disinfection solutions having a principle disinfection agent such as but not limited to bleach, hydrogen peroxide, chlorine, alcohol, quaternary ammonium compounds or ozone. In any of such cases, the liquid and vapor germicides may be aqueous or non-aqueous. It is noted that although germicidal sources which are configured to generate a liquid, vapor, gaseous or plasma germicide that is molecularly configured to deactivate or kill microorganisms are discussed in detail above, the apparatuses considered herein may, in some embodiments, include a germicidal source configured to generate a liquid, vapor, gaseous or plasma germicide which imparts its deactivation or killing functionality by the manner in which it is used, such as via boiling water, steam or heated air. In any case, examples of apparatuses which may be configured to disperse liquid, vapor, gaseous, or plasma germicides include but are not necessarily limited to liquid sprayers, foggers, plasmas torchers and misting systems including wet and dry mist systems. As used herein, the term "mist" refers to a suspension of minute globules of a liquid in a gas. For use herein, a germicidal mist is categorized as a liquid germicide.

As noted above, a germicidal source of the apparatuses described herein may, in some embodiments, be a device configured to generate germicidal light. The term "germicidal light" refers to light which is capable of deactivating or killing microorganisms, particularly disease carrying and/or disease producing microorganisms (a.k.a., germs). Ranges of light which are known to be germicidal include ultraviolet light between approximately 200 nm and approximately 320 nm, particularly 220 nm and between 260 nm and 265 nm, and visible violet-blue light (also known as high-intensity narrow-spectrum (HINS) light) between approximately 400 nm and approximately 470 nm, particularly 405 nm. In some embodiments, a germicidal light source may generate ranges of light which are not germicidal such as but not limited to visible light greater than approximately 500 nm, but such capability will not deter from the reference of the light sources being germicidal. Examples of germicidal light sources which may be configured to generate ultraviolet light and/or HINS light include discharge lamps, light emitting diode (LED) solid state devices, and excimer lasers. HINS lamps are generally constructed of LEDs.

A discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the discharge lamps which may be considered for the germicidal sources described herein include gas-discharge lamps as well as surface-discharge lamps. Discharge lamps may be further characterized by the type of gas/es employed and the pressure at which they are operated. The discharge lamps which may be considered for the germicidal sources described herein may include those of low pressure, medium pressure and high intensity. In addition, the gas/es employed may include helium, neon, argon, krypton, xenon, nitrogen, oxygen, hydrogen, water vapor, carbon dioxide, mercury vapor, sodium vapor and any combination thereof. In some embodiments, various additives and/or other substances may be included in the gas/es. In any case, the discharge lamps considered for the germicidal sources described herein may include those which generate continuous light and those which generate light in short durations, the latter of which are often referred to as flashtubes or flashlamps. Flashtubes or flashlamps that are used to supply recurrent pulses of light are often referred to as pulsed light sources.

A commonly used gas-discharge lamp used to produce continuous light is a mercury-vapor lamp, which may be considered for some of the germicidal sources described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the germicidal sources described herein is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm). In addition, a xenon flashtube can provide relatively sufficient intensity in the spectrum which is known to be optimally germicidal (i.e., 220 nm and/or between approximately 260 nm and approximately 265 nm). Moreover, a xenon flashtube generates an extreme amount of heat, which can further contribute to the deactivation and/or killing of microorganisms.

Although they are not readily available on the commercial market to date, a surface-discharge lamp may be considered for some of the germicidal sources described herein as noted above. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, offer greater UV efficiency as well as longer lamp life as compared to xenon flashtubes. It is noted that the aforementioned descriptions and comparisons of a mercury-vapor lamp, a xenon flashlamp, and a surface discharge lamp in no way restrict the germicidal sources described herein to include such lamps. Rather, the aforementioned descriptions and comparisons are merely provided to offer factors which one skilled in the art may contemplate when selecting a discharge lamp for a germicidal source, particularly depending on the objective and application of the apparatus.

As noted above, the apparatuses described herein include configurations for selectively conducting different disinfection modes exterior and interior to the apparatus, particularly room/area disinfection processes exterior to the apparatus and object and/or air disinfection processes interior to the apparatus. As used herein, the term "room/area disinfection" refers to the cleansing of a space which is suitable for human occupancy so as to deactivate, destroy or prevent the growth of disease-carrying microorganisms in the area. The phrase "a space which is suitable for human occupancy" as used herein refers to a space in which an adult human being of average size may comfortably occupy for at least a period of time to eat, sleep, work, lounge, partake in an activity, or complete a task therein. In some cases, spaces suitable for human occupancy may be bounded and include a door for entering and exiting the room. In other cases, a space suitable for human occupancy may be an area with indeterminate boundaries. Examples of spaces which are suitable for human occupancy include but are not limited to single patient rooms, multiple occupancy patient rooms, bathrooms, walk-in closets, hallways, bedrooms, offices, operating rooms, patient examination rooms, waiting and/or lounging areas and nursing stations.

Since the apparatuses described herein are specific to being able to perform room/area disinfection processes, the apparatuses include configurations to facilitate room/area disinfection when their germicidal sources are arranged to disperse germicide/s exterior to the apparatuses. More specifically, the apparatuses described herein include configurations to distribute an effective amount of germicide in a spacious manner to an ambient of a room in which the apparatus is arranged to maximize the number of surfaces and objects disinfected in the room. The apparatuses may be of any shape, size, or configuration in which to achieve such an objective. For example, a configuration which may be considered for the apparatuses described herein is to position the germicidal source within the apparatus to distribute a germicide approximately 360° around the source, such as described in reference to FIGS. 1 and 13. In such cases, the apparatuses may be void of a component sufficient to block the germicide approximately 360° around the apparatus such that germicide emitted from the germicidal source substantially encircles the apparatus. In other embodiments, however, apparatuses having configurations which enable both interior and exterior disinfection modes may be configured to distribute a germicide less than 360° around its exterior during exterior disinfection modes, such as described in reference to FIG. 11.

Yet another configuration for the apparatuses described herein to aid in the distribution of a germicide in a room or area is for the apparatus to be automated to move through the room or area while the germicidal source is projecting germicide into an ambient of the room or area. For instance, the apparatuses described herein may include motorized wheels and processor-executable program instructions for activating the motorized wheels in accordance with a predetermined route and/or in response to sensors to maneuver around obstacles in the room or area while the germicidal source is emitting germicide/s. Other examples of configurations specific to facilitating area/room disinfection which may be included in the apparatuses described herein are disclosed in U.S. application Ser. No. 13/706,926 filed Dec. 6, 2012 and Ser. No. 13/708,208 filed Dec. 7, 2012 and International Application No. PCT/US2014/059698 filed Oct. 8, 2014, all of which are incorporated herein by reference as if set forth fully herein. Other configurations of area/room disinfection apparatuses, however, may be additionally or alternatively employed for apparatuses described herein. Furthermore, although the apparatuses described herein are not necessarily bound to use in rooms and areas of a particular size, in some cases the apparatuses described herein may be particularly configured for partitioned area of at least approximately 4 m$^3$.

In some embodiments, the apparatuses described herein may include configurations to distribute an effective amount of germicide to achieve a between a 2-log and 4-log reduction in bacterial contamination on surfaces within a room or area that are greater than 1 meter or even 2 or 3 meters from the germicidal source. Configurations used to generate such an effect generally depend on the configuration of the germicidal source, particularly the size of the germicidal source, the intensity and/or frequency at which the germicide is dispersed and the orientation of the germicidal source in the apparatus. In general, the germicidal sources considered herein may, in some embodiments, be any shape, size, orientation or configuration and may be conducted at parameters to achieve a desired reduction in bacterial contamination on surfaces within a room or area that are greater than 1 meter or even 2 or 3 meters from the apparatus. An example of an orientation of a germicidal source which may aid in achieving such an effect is that the germicidal source may be vertically arranged (e.g., the germicidal source may be arranged lengthwise substantially perpendicular to a horizontal plane of the support structure) to aid in distributing the germicide greater distances within a room or area.

In some cases, the apparatuses described herein may utilize configurations of other components in the apparatus (i.e., other than the configurations of the germicidal source) to aid in achieving a desired reduction in bacterial contamination on surfaces within a room or area that are greater than 1 meter or even 2 or 3 meters from the germicidal source. For example, the apparatuses described herein may, in some embodiments, include an actuator coupled to the germicidal source and processor-executable program instructions for activating the actuator to move the germicidal source while the germicidal source is projecting germicide into an ambient of a room or area to aid in the distribution of germicide in a room or area. More specifically, the germicidal source may be moved in vertical, horizontal and/or diagonal directions via the actuator while the germicidal source is projecting germicide into an ambient of a room or area.

Regardless of any specific germicidal efficacy objective for the apparatuses described herein and the component configurations used to achieve such an objective, a component which is often included in room disinfection apparatuses and which may be included in the apparatuses disclosed herein is a movement detection sensor and/or a room/area occupancy sensor, such as a motion sensor, a thermal sensor, a Doppler sensor, or a photo recognition sensor. In particular, the apparatuses described herein may include program instructions to inhibit or terminate activation of a power supply circuit to the germicidal source upon detecting movement and/or occupancy in the area/room in which the apparatus is arranged. Additional program instructions utilizing information from a movement detection sensor and/or a room/area occupancy sensor and which are specific to the configurations of the apparatuses described herein that allow disinfection processes to be performed interior and exterior to the apparatuses are described below in reference to FIGS. 16 and 17.

Turning to FIG. 1, apparatus 20 is shown having germicidal source 22, chamber 24, power circuitry 26, program instructions 28, processor 30, user interface 32, remote user interface 34, base 36 as well as sensors 38 and 48. In general, power circuitry 26, program instructions 28, processor 30, user interface 32, remote user interface 34 and sensors 38/48 may be in electrical communication with each other (via wired or wireless connections) to affect operations of the apparatus. For instance, power circuitry 26 is electrically coupled to germicidal source 22 to operate the germicidal source to generate a germicide and power circuitry 26 is further electrically coupled to processor 30, user interface 32, remote user interface 34 and/or sensors 38/48 to affect the timing at which to operate germicidal source 22. In addition, processor 30 is electrically coupled to program instructions 28 such that the program instructions may be executed by the processor and, in addition, processor 30 is electrically coupled to user interface 32, remote user interface 34 and/or sensors 38/48 to affect operations of such components in accordance with program instructions 28. Other electrical connections may be included in the apparatus 20 between any of the noted components and other components of apparatus 20 to affect operations thereof, particularly to affect the operations described in reference to FIGS. 1-17. For example, power circuitry 26, processor 30, user interface 32, remote user interface 34 and/or sensors 38/48 may be in electrical communication with an air moving device, an air flow regulator, an actuator, other sensors, other germicidal sources or any other components optionally included in the apparatus to affect the operation of the components.

The term "program instructions," as used herein, refers to commands within software which are configured to perform a particular function, such as any of the processes described in reference to FIGS. 2, 6, 7 and 14-17. Program instructions 28 may be implemented in any of various ways, including procedure-based techniques, component-based techniques, and/or object-oriented techniques, among others. For example, program instructions 28 may be implemented using ActiveX controls, C++ objects, JavaBeans, Microsoft Foundation Classes ("MFC"), or other technologies or methodologies, as desired. Program instructions 28 may be transmitted over or on a carrier medium such as a wire, cable, or wireless transmission link. It is noted program instructions 28 may include program instructions for performing processes other than those specifically described herein and, therefore, the apparatuses described herein are not limited to having program instructions for performing the operations described in reference to FIGS. 2, 6, 7 and 14-17. In general, program instructions 28 may be stored with a storage medium within the apparatuses described herein. The term "storage medium", as used herein, refers to any electronic medium configured to hold one or more set of program instructions, such as but not limited to a read-only memory, a random access memory, a magnetic or optical disk, or magnetic tape.

As shown in FIG. 1, germicidal source 22 may be supported and moveable in and out of chamber 24 via support members 40. In particular, support members 40 may be coupled to a lower portion of germicidal source 22 and may be configured to draw germicidal source 22 into chamber 24 as denoted by the dotted line version of germicidal source 22 and the doubled arrow vertical line adjacent germicidal source 22 in FIG. 1. In general, apparatus 20 may include any number of support members to support and/or move germicidal source 22 and, thus, apparatus 20 need not be limited to having two support members 40 as shown in FIG. 1. Furthermore, apparatus 20 need not be limited to having support members coupled to the bottom of germicidal source 22 as shown in FIG. 1. In particular, apparatus 20 may additionally or alternatively include components coupled to and/or configured to engage the sidewalls and/or top surfaces of germicidal source 22 to support and/or affect its movement in and out of chamber 24. For instance, germicidal source 22 and chamber 24 may respectively include engageable notches and protrusions or vice versa to support and affect movement of germicidal source 22 in and out of chamber 24. In addition or alternatively, apparatus 20 may include a component coupled to the top portion of germicidal source 22 to support the germicidal source and, in some cases, to offer a manner in which to pull and push the germicidal source in and out of chamber 24. In any case, components used to affect movement of germicidal source 22 may be configured in any manner known to achieve such a function, such as but not limited to displaceable components (e.g., rigid unmalleable bars which may be displaced within apparatus 20), retractable (i.e., collapsible or nestable) bars, and sliding tracks. In some cases, an actuator (i.e., a motorized component) may be used to affect automated movement of germicidal source 22. However, in other cases, movement of germicidal source 22 may be manually affected by a user of apparatus 20.

As denoted by the double arrow vertical line adjacent chamber 24 in FIG. 1, apparatus 20 may, in some cases, be configured to move chamber 24 up and down. Such a configuration may be in addition to or alternative to having a component to affect the movement of germicidal source 22 within apparatus 20. In particular, apparatus 20 need not be restricted to having germicidal source 22 displaceable in order to contain it and extend it out of chamber 24. Rather, apparatus 20 may additionally or alternatively include configurations to move chamber 24 up and down such that germicidal source 22 may be encased therein for at least one mode of operation of apparatus 20 as well as have at least a portion thereof extend exterior to the chamber for at least a different mode of operation of apparatus 20. Configurations to allow movement of chamber 24 within apparatus 20 may include any configuration known to achieve such a function, such as but not limited to displaceable components coupled to the bottom, sides and/or top of chamber 24, retractable bars coupled to the bottom, sides and/or top of chamber 24, sliding tracks between the sides of chamber 24 and germicidal source 22, and/or sliding tracks between the sides of chamber 24 and a component coupled to the exterior of chamber 24. In some cases, an actuator (i.e., a motorized component) may be used to affect automated movement of chamber 24. However, in other cases, movement of chamber 24 may be manually affected by a user of apparatus 20.

Regardless of whether chamber 24 and/or germicidal source 22 is configured to move within apparatus 20, the movement of germicidal source 22 and/or chamber 24 is to either contain the germicidal source 22 within chamber 24 or extend germicidal source 22 outside of chamber 24. As set forth in more detail below, in embodiments in which germicidal source 22 is contained within chamber 24, the movement germicidal source 22 and/or chamber 24 may concurrently encase the germicidal source within the chamber. In particular, apparatus 20 may, in some embodiments, be configured such that germicidal source 22 is encased within chamber 24 upon being contained therein (e.g., via closure of a door over port 42 or an upper portion of a housing comprising germicidal source 22 sealing port 42). In other cases, encasing chamber 24 may be conducted after germicidal source 22 is contained therein. As used herein, the term "contained" refers to residing within the boundaries of storage unit. On the contrary, the term "encased" refers to being enclosed. Furthermore, it is noted germicidal source 22 may be partially or fully extended outside of chamber 24 for disinfection processes conducted exterior to apparatus 20. In particular, all of germicidal source 22 or only a portion of germicidal source 22 may be positioned exterior to chamber 24 for area/room disinfection processes conducted by the apparatus.

As shown in FIG. 1 and noted above, apparatus 20 may include base 36. In general, base 36 may be configured to support chamber 24 and/or support members 40. Any configuration known to achieve such function may be used for base 36, including but not limited to a plate, an annular ring, or a set of support legs (e.g., similar to legs of a table). Inclusion of base 36 may be particularly useful in embodiments in which apparatus 20 includes configurations to move chamber 24. However, base 36 may still be useful in apparatus 20 in embodiments in which apparatus 20 is not configured to move chamber 24. For example, in some of such latter cases, base 36 may form a part (i.e., the floor) of chamber 24. In addition or alternatively and regardless of whether apparatus is configured to move chamber 24, base 36 may be configured such that the height of apparatus 20 may be within design specifications, particularly if the size of chamber 24 is restricted to limit the distance at which a germicide travels to disinfect an air stream flowing therethrough or an object placed inside the chamber as described in more detail below. In yet some cases, however, base 36 may be omitted from apparatus 20. In particular, chamber 24 may serve as a base for apparatus 20 in some embodiments. In any case, optional features for the apparatuses considered herein include wheels and/or a handle to affect portability for the apparatus and either may be coupled to chamber 24, base 36 or any other component of apparatus 20, depending on the design specifications of the apparatus.

As shown in FIG. 1, power circuitry 26, program instructions 28, processor 30 and user interface 32 may be arranged in chamber 24. In some embodiments, however, it may be advantageous to arrange one or more of power circuitry 26, program instructions 28, processor 30 and user interface 32 in base 36 or a different structure of apparatus 20 distinct from chamber 24 (such as a structure arranged adjacent to or above chamber 24) to avoid exposure of such components to a germicide generated by germicidal source 22 or byproducts of the germicide generation. For example, in embodiments in which germicidal source 22 is an ultraviolet (UV) lamp, the UV light and the heat generated from the lamp may degrade power circuitry 26, program instructions 28, processor 30 and user interface 32 or even housings storing such components in chamber 24. Likewise, in embodiments in which germicidal source 22 is a source of a chemical vapor, liquid, and/or gas (e.g., hydrogen peroxide vapor), exposure of the chemical and/or moisture generated from the lamp may degrade power circuitry 26, program instructions 28, processor 30 and user interface 32 or even housings storing such components in chamber 24. Alternatively, power circuitry 26, program instructions 28, processor 30 and/or user interface 32 may be stored in housings in chamber 24 which are configured to withstand the heat, moisture and chemicals generated by germicidal source 22.

In some cases, the generation of heat and moisture as well as chemical dispersion within chamber 24 may be detrimental to chamber 24 itself. In addition, heat and moisture may reduce the germicidal efficacy of germicidal source 22 within chamber 24. Thus, chamber 24 may, in some cases, include configurations to dissipate or remove heat, moisture and chemicals generated by germicidal source 22 regardless of whether power circuitry 26, program instructions 28, processor 30 and/or user interface 32 are arranged therein. For example, chamber 24 may, in some embodiments, include heat shields within its interior and/or along one or more its exterior sidewalls to avoid the exterior of chamber 24 from getting too hot, particularly too hot to touch. In addition or alternatively, chamber 24 may include one or more heat sinks within its interior and/or along one or more its exterior sidewalls. Furthermore, chamber 24 may, in some cases, include a cooling device within its interior for reducing the temperature therein. Moreover, chamber 24 may additionally or alternatively include a dehumidifier and/or the interior sidewalls of chamber 24 may additionally or alternatively comprise chemically resistant materials. Moreover, chamber 24 may additionally or alternatively include filtered outlets to discharge heat, moisture and chemicals dispersed therein. In cases in which chemical vapor, gases or liquids are generated in chamber 24, the filtered outlets may include filters to capture and/or neutralize hazardous elements/components of the chemical/s.

Regardless of whether chamber 24 includes configurations to dissipate or remove heat, moisture and chemicals generated by germicidal source 22 therein, apparatus 20 is configured such that germicide projected from germicidal source 22 is substantially contained in chamber 24 when germicidal source 22 is encased in the chamber. Such configurations of apparatus 20 may include configurations of chamber 24 to contain the germicide. For example, the sidewalls of chamber 24 may be made of solid impervious material/s and the seams adjoining the sidewalls of chamber 24 may be sealed. In addition, any air inlets and air outlets of chamber 24 (which as described in more detail below affect apparatus 20 to conduct air disinfection within chamber 24) may include filters by which to prevent the release of germicide therethrough. Furthermore, as described in more detail below in reference to FIG. 3, chamber 24 may, in some cases, include a door at port 42 and/or a door at a loading port through which objects may be loaded for an object disinfection process within chamber 24. In such cases, the door/s may be configured to substantially prevent release of the germicide projected from germicidal source 22 when the germicidal source is contained in the chamber and the door/s are closed. In other cases, chamber 24 may, in some embodiments, include a seal at port 42 through which germicidal source 22 or the housing containing germicidal source 22 may slidingly pass upon moving the germicidal source and/or the chamber to affect the germicidal source in and out of the chamber. In such cases, chamber 24 and/or germicidal source 22 may be configured to terminate its movement for interior disinfection processes such that an upper portion of the housing comprising germicidal source 22 is in contact with the seal at port 42 to encase the germicidal source within chamber 24.

In some cases, configurations of apparatus 20 to substantially contain germicide projected from germicidal source 22 in chamber 24 when germicidal source 22 is encased in the chamber may include configurations of other components of apparatus 20 (i.e., other than chamber 24). For example, the top portion of germicidal source 22 or the housing comprising germicidal source 22 may include a seal along its exterior sidewalls (particularly around its top surface) which comes into contact with port 42 when the germicidal source is positioned within chamber 24. In such cases, chamber 24 and/or germicidal source 22 may be configured to terminate its movement for interior disinfection processes such that the seal is in contact with port 42 to encase the germicidal source within chamber 24. In addition or alternatively, apparatus 20 may include a component disposed above germicidal source 22 with portions which mate with exterior portions of chamber 24 adjacent to port 42, such as described in more detail below in reference to FIG. 5.

In some cases, chamber 24 may be opaque, particularly in embodiments in which germicidal source 22 includes a germicidal lamp which produces very bright visible light and/or is a pulsed light source run at a pulse frequency between approximately 3 Hz and approximately 50 Hz (i.e., the frequency range which is generally considered to induce seizures). Xenon flashlamps are often run at parameters which induce one or both of these effects and, thus, it may be advantageous for chamber 24 to be opaque when germicidal source 22 is a xenon flashlamp, depending on the parameters at which the flashlamp is operated. In other embodiments, however, chamber 24 may be transparent to visible light (e.g., chamber 24 may be made of glass), even in embodiments in which germicidal source 22 includes a xenon flashlamp. In particular, it has been found that xenon flashlamps run at frequencies of 50 Hz and greater generate light at an intensity which is not generally considered disturbing and, thus, germicidal source 22 may, in some cases, include a xenon flashlamp (or any other type of germicidal source) when chamber 24 is transparent to visible light. A description of xenon flashlamps run at frequencies of 50 Hz and greater as well as other configurations of lamp assemblies configured to produce a collective stream of continuous visible light or a collective stream of visible light pulsed at a frequency greater than 50 Hz are disclosed in U.S. Patent Application Ser. No. 62/052,036 filed on Sep. 18, 2014, which is incorporated by reference as if set forth fully herein. It is noted that any of the lamps and systems of lamps described in U.S. Patent Application Ser. No. 62/052,036 may be used as a germicidal source for the apparatuses described herein.

As described above, germicidal source 22 and/or chamber 24 may be repositionable within apparatus 20 and, more specifically, may be linearly displaceable within apparatus 20 such that germicidal source 22 may be contained within chamber and may be at least partially arranged exterior to the chamber for respectively different modes of operation for the apparatus. As further described above, the different modes of operation are room/area disinfection processes conducted exterior to the apparatus and object and/or air disinfection processes conducted interior to the apparatus. To facilitate such dual functionality, chamber 24 includes port 42 in linear alignment with germicidal source 22 and which is dimensionally configured to receive germicidal source 22. In addition, program instructions 28 include code executable by processor 30 for activating power circuitry 26 to operate germicidal source 22 when the germicidal source extends outside chamber 24 as shown by projected germicide 44 in FIG. 1 and by block 50 in FIG. 2 which depicts some of the instructions that may be included in program instructions 28. Furthermore, program instructions 28 includes code executable by processor 30 for activating power circuitry 26 to operate germicidal source 22 when the germicidal source is encased within chamber 24 as shown by projected germicide 46 in FIG. 1 and by block 60 in FIG. 2. In some cases, program instructions 28 may include code executable by processor 30 for activating power circuitry 26 to operate germicidal source 22 when the germicidal source extends outside chamber 24 by a predetermined distance for safety precautions and/or or to ensure optimum germicide dispersal for room/area disinfection processes.

In some embodiments, program instructions 28 for activating power circuitry 26 when germicidal source 22 extends outside chamber 24 may include the same instructions for operating germicidal source 22 as the program instructions for activating power circuitry 26 when germicidal source 22 is encased in chamber 24. In other cases, however, program instructions 28 may include different instructions for activating power circuitry 26 in relation to whether germicidal source 22 extends outside chamber 24 or in encased in chamber 24. For example, program instructions 28 may, in some embodiments, include code executable by processor 30 for activating power circuitry 26 to respectively supply different amounts of power to germicidal source 22 when germicidal source 22 is not encased with chamber 24 and when germicidal source 22 is encased with chamber 24 as respectively denoted in blocks 52 and 62 of FIG. 2. In particular embodiments, program instructions 28 may include code executable by processor 30 for activating power circuitry 26 to supply a lower amount of power to germicidal source 22 when germicidal source 22 is encased with chamber 24 than when germicidal source 22 is not encased with chamber 24. In particular, the air and object disinfection processes conducted within chamber 24 have a much shorter distance requirements to disinfect their target medium than room/area disinfection processes conducted when germicidal source 22 is exterior to chamber 24, and, thus, the germicide need not be projected at as high of an intensity.

Another variation regarding the activation of power circuitry 26 to supply power to germicidal source 22 when the germicidal source is not encased or is encased within chamber 24 includes a variation in the duration the power circuitry 26 is activated as respectively denoted in blocks 54 and 64 of FIG. 2. In particular, an object disinfection process within chamber 24 may require less time to achieve a desired reduction in bacterial contamination on objects within chamber 24 versus a room/area disinfection process. As such, program instructions 28 may, in some embodiments, include code executable by processor 30 for activating power circuitry 26 to supply power to germicidal source 22 for a shorter amount of time when germicidal source 22 is encased with chamber 24 than when germicidal source 22 is not encased with chamber 24. In yet other embodiments, program instructions 28 may include code executable by processor 30 for activating power circuitry 26 to supply power to germicidal source 22 for a longer amount of time when germicidal source 22 is encased with chamber 24 than when germicidal source 22 is not encased with chamber 24. In particular, an air disinfection process conducted interior to an apparatus may be run for a longer duration than an area/room disinfection process conducted exterior to an apparatus since the volume of air disinfected for a given amount of time during an interior air disinfection process is considerably less than in an exterior area/room disinfection process.

Yet another variation regarding the activation of power circuitry 26 to supply power to germicidal source 22 when the germicidal source is not encased or is encased within chamber 24 includes a variation in the pulse frequency at which power circuitry 26 operates a flashlamp (i.e., when germicidal source 22 is a flashlamp) as respectively denoted in blocks 56 and 66 of FIG. 2. In particular, as noted above, the germicide projected for air and object disinfection processes conducted within chamber 24 need not be as intense as room/area disinfection processes conducted when germicidal source 22 is exterior to chamber 24. Lower intensity pulses in flashlamps generally allow flashlamps to be pulsed at higher frequencies since less accumulated energy is needed. Given the relatively small volume of space within chamber 24 for air and object disinfection processes, higher frequencies of germicidal light may shorten the time at which to achieve a desired disinfection objective and/or may increase germicidal efficacy for such processes. Thus, program instructions 28 may, in some embodiments, include code executable by processor 30 for activating power circuitry 26 to apply a trigger voltage to germicidal source 22 at a higher frequency when germicidal source 22 is encased with chamber 24 than when germicidal source 22 is not encased with chamber 24.

In any case, apparatus 20 may include sensor 38 to determine whether germicidal source 22 is encased within chamber 24 and/or to determine whether germicidal source 22 is not encased within chamber 24. For example, sensor 38 may, in some embodiments, be fixedly arranged within chamber 24 at a location such that when germicidal source 22 comes into contact with sensor 38, the germicidal source 22 is contained in chamber 24. In such cases, sensor 38 may be arranged at a location which further indicates germicidal source 22 is not contained in chamber 24 when germicidal source 22 is not in contact with the sensor. In other cases, sensor 38 may be attached to germicidal source 22 and configured to touch contacts disposed within or on chamber 24 at locations which respectively indicate germicidal source 22 is encased and not encased within the chamber such as shown in FIG. 1. Further yet, sensor 38 may be disposed within or exterior to chamber 24 at a location wherein upon touching a contact on germicidal source 22, at least a portion of the germicidal source extends out of the chamber and, in some cases, by a predetermined distance. It is noted that the aforementioned configurations of sensor 38 are examples and other configurations of sensors and/or sensor systems may additionally or alternatively employed within apparatus 20 to determine whether germicidal source 22 is encased within chamber 24 and/or to determine whether germicidal source 22 is not encased within chamber 24. For example, sensor 38 is not limited to contact sensor technology, but rather could include light beam sensor technology or other types of sensors.

As noted above, apparatus 20 may further include sensor 48. Sensor 48 is a sensor configured to detect movement and/or room/area occupancy within an ambient of apparatus 20, such as a motion sensor, a thermal sensor, a Doppler sensor, or a photo recognition sensor. Although sensor 48 is shown attached to base 36 in FIG. 1, apparatus 20 is not limited to such placement. In particular, sensor 48 may be coupled to any portion of apparatus 20. Furthermore, apparatus 20 is not limited to having a single motion and/or room/area occupancy sensor. Rather, apparatus 20 may include multiple motion and/or room/area occupancy sensors in some embodiments, all of which may be of the same type or may include different types.

As shown in FIG. 1 and mentioned above, apparatus 20 may include user interface 32 and, in some cases, remote user interface 34. Remote user interface 34 may be integrated into a variety of devices including but not limited to hand held communication devices (i.e., pagers, telephones, etc.) and computers. In general, user interface 32 and remote user interface 34 may include input controls to affect operation of apparatus 20, such as but not limited to a start and stop button to enable a user to start and terminate an operation of apparatus 20. Configurations for input controls to affect operation of apparatus 20 as well as configurations to input other information into user interface 32 and remote user interface 34 may include any of those known in the art, including but not limited to touch sensor means, audible means, and graphical user interfaces. As set forth in more detail below, user interface 32 and/or remote user interface 34 may, in some embodiments, include input controls allowing selection of different disinfection modes conducted by the apparatus. In particular, user interface 32 and/or remote user interface 34 may include input controls allowing selection of a disinfection mode for primarily disinfecting a medium (such as objects and/or air) inside chamber 24 and further a disinfection mode for primarily disinfecting a medium exterior to chamber 24.

In any case, user interface 32, and in some cases remote user interface 34, may additionally be configured to receive signals and output information pertaining to such signals to a user in informative manner. Configurations to output the information may include any visual display or audible means known in the art. Examples of information output by user interface 32 and/or remote user interface 34 may include but are not limited to notices to move germicidal source 22 and/or chamber 24 to a position to affect a particular disinfection mode. In other cases, movement of germicidal source 22 and/or chamber 24 may be automated and may be activated in response to a selected disinfection mode via user interface 32 and/or remote user interface 34.

As described above, apparatus 20 is configured to allow different modes of operation to be conducted, specifically room/area disinfection processes exterior to the apparatus and object and/or air disinfection processes interior to the apparatus. Some of such configurations include, as described above, configurations of germicidal source 22 and/or other components of apparatus 20 to distribute an effective amount of light in a spacious manner to an ambient of a room when germicidal source 22 is exterior to chamber 24. Additional configurations, as described above, include a port within chamber 24 to receive germicidal source 22 and program instructions 28 for activating power circuitry 26 to operate germicidal source 22 when the germicidal source is either encased within chamber 24 or exterior to the chamber. Other configurations particularly to facilitate object and/or air disinfection processes interior to the apparatus are shown and described in reference to FIGS. 3 and 4.

In particular, FIG. 3 illustrates an example configuration of chamber 24 including loading port 70 and door 72 for the loading of objects into the interior of chamber 24. In some cases, chamber 24 may include shelves 74 as shown in FIG. 3 or some other support structure (e.g., perforated basket/s) within its interior for objects to be placed on. Any number of support structures (e.g., shelves and/or baskets) may be used. In some embodiments, particularly when germicidal source 22 includes a germicidal light source, the support structures may be made of a material transparent to the germicidal light generated by germicidal source 22 such that surfaces in contact with the support structures may be disinfected. In any case, the support structures may be arranged anywhere within chamber 24 except the region which germicidal source 22 is to occupy. In some embodiments, support structures may be attached to the interior side of door 72. In any case, chamber 24 may, in some embodiments, include multiple loading ports and accompanying doors, particularly on different sides of chamber 24. For example, chamber 24 may, in some cases, include loading ports and accompanying doors on opposing sides of the chamber. It is noted that although door 72 is shown as a hinged door, the apparatuses described herein are so limited. In particular, door 72 may alternatively be a sliding door or a removable lid. Similarly, door 76 shown in FIG. 3 over port 42 may be a hinged or sliding door or a removable lid. In any case, door 72 and/or door 76 may be manually actuated and/or apparatus 20 may include one or more actuators to automate movement of the doors.

Figure 4:
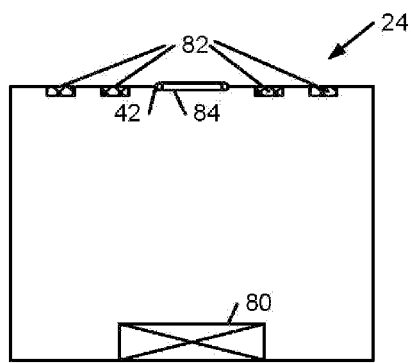
FIG. 4 illustrates a cross-sectional view of an example chamber for the apparatus depicted in FIG. 1.

Yet another configuration to facilitate air disinfection processes interior to apparatus 20 is to include an air moving device within the chamber such as shown in the example configuration of chamber 24 in FIG. 4. In particular, FIG. 4 illustrates a cross-sectional view of the interior of chamber 24 including air moving device 80 and air outlets 82. In general, air moving device 80 is configured to draw in air from the ambient of apparatus 20 and air outlets 82 include filters to prevent germicide generated from germicidal source 22 inside chamber 24 from escaping chamber 24. Air moving device 80 in chamber 24 of FIG. 4 is arranged within or is in alignment with an air inlet of chamber 24. In other embodiments, however, air moving device 80 may be arranged apart from air inlet/s to chamber 24. For example, air moving device 80 may be arranged adjacent to air outlets 82. Furthermore, the placement of air inlet/s, air moving device 80 and air outlets 82 as well as the quantity thereof in chamber 24 may differ from what is depicted in FIG. 4. In particular, chamber 24 may include any number of air inlets, air moving devices and air outlets and they may be arranged at any location along the sidewalls, floor and ceiling of chamber 24, depending on the design specifications of chamber 24 and apparatus 20.

It is further noted when air moving device 80 and/or an air inlet is arranged within the floor of chamber 24, apparatus 20 is configured such that air moving device 80 and/or the air inlet can readily access and draw in air from an ambient of the apparatus. For example, base 36, in such cases, may be annular and suspended above a floor of a room/area in which the apparatus is arranged or base 36 may include a set of support legs (e.g., similar to legs of a table). Alternatively, chamber 24 may be suspended above base 36. In any case, filtering air coming into chamber 24 may improve the germicidal efficacy of germicidal source 22 in chamber 24 and, thus, in some embodiments, the air inlet/s of chamber 24 may include filters. In some cases, apparatus 20 may include dehumidifiers and/or cooling devices within chamber 24 and/or adjacent to air inlet/s of chamber 24 (i.e., adjacent the air intake or air outtake of the inlet/s) to control the humidity and temperature of the air disinfected in the chamber by germicidal source 22. In particular, controlling the humidity and/or temperature may improve the germicidal efficacy of germicidal source 22 in chamber 24 in addition to or alternative to removal of particulate material in the air by a filter. In any case, air moving device 80 may include any device configured to cause air to flow, including but not limited to a fan or a turbine. In cases in which a turbine is used in the apparatuses described herein, the turbine may be used to supply power to one or more components of the apparatuses, including any of the components described herein or a battery of the apparatus.

FIG. 4 further illustrates a variation to door 76 of FIG. 3 for closing port 42 when germicidal source 22 is contained in chamber 24. In particular, FIG. 4 illustrates seal 84 along the circumference of port 42. As described above, a housing comprising germicidal source 22 may slidingly pass through port 42 against seal 84 upon being drawn into chamber 24. In such cases, apparatus 20 may be configured such that an upper portion of the housing is in contact with seal 84 such that port 42 is closed when germicidal source 22 has been placed in position within chamber 24 to conduct an air and/or object disinfection process. In some embodiments, the device used to close port 42 (such as a door as described above in reference to FIG. 3 or an upper portion of a housing comprising germicidal source 22 as described in more detail below in reference to FIG. 4) may include an air outlet with a filter to prevent germicide from escaping chamber 24. In cases in which germicidal source 22 includes an ultraviolet lamp, the device used to close port 42 may include an ozone filter, such as described below in reference to FIG. 5.

In some embodiments, chamber 24 may include a plenum extending between port 42 and the opposing side of chamber 24 when air moving device 80 and/or an air inlet is arranged in the vicinity of the opposing side of chamber 24. In general, the plenum is sized to accommodate germicidal source 22 as well as a finite amount of space along the length of the germicidal source such that air may be routed in close proximity to the germicidal source. Having such a plenum in chamber 24 will reduce the volume of air disinfected for a given flow rate of air through the chamber, but may offer higher germicidal efficacy as compared embodiments in which a plenum is not used. In cases in which germicidal source 22 includes a germicidal light source, the plenum may be made of a material transparent to the germicidal light generated by germicidal source 22 such that objects placed in chamber 24 exterior to the plenum may be disinfected at the same time air is disinfected within the plenum.

Segregating portions of chamber 24 for air disinfection and objection disinfection via plenum may be advantageous in some cases to prevent objects from being displaced by the air flow through the chamber. In particular, in some cases, the air flow through chamber 24 may be high enough to move objects placed within chamber 24 and, in some embodiments, the movement of the objects may be great enough to damage the objects, the chamber and/or germicidal source 22. In yet other embodiments, however, chamber 24 may not include a plenum. In particular, the air flow through chamber 24 may not be great enough to move objects therein or chamber 24 may not be used for object disinfection. In yet other cases, germicidal source 22 may include a plenum as part of a housing surrounding its source of germicide, such as described below in reference to the example configuration of germicidal source 22 in FIG. 5.

It is noted that any of the features depicted in FIGS. 3 and 4 may be combined and/or variations of the features may be employed. For example, chamber 24 may, in some cases, have a loading port, a door and an air moving device. In addition or alternatively, chamber 24 may have shelves of different size, shape or orientation than what is depicted in FIG. 3. Consequently, chamber 24 is not limited to the depictions of FIGS. 3 and 4. Furthermore, it is noted that any of the components described in FIG. 1 for chamber 24 may be included in the configurations described in reference FIGS. 3 and 4. For instance, any of the chamber configurations described in reference to FIGS. 3 and 4 may include power circuitry 26, program instructions 28, processor 30, user interface 32, sensors 38, and/or support member 42. The noted components are not shown in FIGS. 3 and 4 to simplify the drawings, particularly to emphasize component configurations which may facilitate object and/or air disinfection processes interior to the apparatus.

Figure 5:
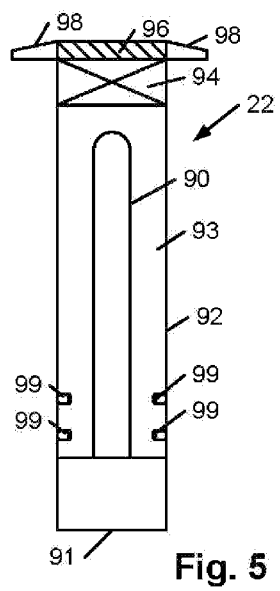
FIG. 5 illustrates an example germicidal source assembly for the apparatus depicted in FIG. 1.

As noted above, FIG. 5 illustrates a configuration of germicidal source 22 having a plenum as part of a housing surrounding its source of germicide. More specifically, FIG. 5 illustrates an example configuration of germicidal source 22 having germicidal light source 90 disposed within circumjacent barrier 92 and between air inlet 91 and air moving device 94, forming plenum 93 around germicidal light source 90. Circumjacent barrier 92 is made of a material transparent to the germicidal light generated by germicidal light source 90 such that the germicidal light may be transmitted exterior to germicidal source 22. Air moving device 94 draws air into plenum 93 through air inlet 91 and discharges through air outlet 96. In an alternative embodiment, air moving device 94 may be arranged in proximity to air inlet 91. In any case, air inlet 91 may include a filter to remove particular matter from an incoming air stream. As noted above in reference to FIG. 4, removing particulate material from air may improve the germicidal efficacy of an air disinfection process performed within apparatus 20. Similar to the air inlets described in reference to chamber 24 of FIG. 4, germicidal source 22 may, in some cases, include dehumidifiers and/or cooling devices adjacent to its air inlet (i.e., adjacent the air intake or air outtake of the inlet) to control the humidity and temperature of the incoming air to improve the germicidal efficacy of germicidal source 22 in addition to or alternative to removal of particulate material in the air by a filter.

In some cases, air outlet 96 may include an ozone reducing device, such as a carbon filter or a device which produces free radicals catalysts that covert ozone to diatomic oxygen. In particular, ozone may, in some cases, be created as a byproduct from the use of germicidal light source 92, specifically if the lamp generates ultraviolet light of wavelengths shorter than approximately 240 nm since such a spectrum of UV light causes oxygen atoms of oxygen molecules to dissociate, starting the ozone generation process. Ozone is a known health and air quality hazard and, thus, the release of it by devices is regulated. It is also known that ozone is an effective germicidal agent and deodorizer and, thus, if the amount of ozone to be generated by a discharge lamp is lower than the local/regional exposure limits for ozone, it may be beneficial to exclude an ozone reducing device from air outlet 96. In yet other cases, air outlet 96 may have a portion with an ozone reducing device and a portion without an ozone reducing device and further an air flow regulator to respectively route air through the different portions depending on operating parameters and/or modes of disinfection processes employed by apparatus 20. Examples of air outlets having such features are described in more detail below in reference to FIGS. 9a-10.

Regardless of whether air outlet 96 includes an ozone reducing device, it may, in some cases, be advantageous for air outlet 96 to include an air filter to block light. In particular, in embodiments in which the top portion of germicidal source 22 is used to close port 42 of chamber 24 as described above in reference to FIG. 4, it will be generally advantageous to have the germicidal light blocked through air outlet 96. In this manner, germicidal light generated by germicidal light source 90 may be prevented from being emitted from chamber 24 during disinfection processes conducted interior to the chamber. It yet other embodiments, air outlet 96 need not have any air filter to block light. In particular, apparatus 20 may, in some cases, be configured to encase germicidal source 22 within chamber 24, including a housing surrounding its source of germicide. In such cases, germicidal light generated by germicidal light source 90 may be prevented from being emitted from chamber 24 during disinfection processes conducted interior to the chamber, but may be transmitted into an ambient of apparatus 20 during disinfection processes conducted exterior to the chamber. In any case, the purpose of air inlet 91, air moving device 94, circumjacent barrier 92 and air outlet 96 within germicidal source 22 of FIG. 5 may be two-fold, specifically that they may be together used to cool germicidal light source 90 as well as enable air disinfection during disinfection processes conducted either interior or exterior to the chamber. Furthermore, the configuration of germicidal source 22 in FIG. 5 may prevent objects from being displaced during a disinfection process conducted interior to the chamber as similarly described above for the incorporation of a plenum within chamber in reference to FIG. 4.

In addition to the aforementioned plenum configuration, FIG. 5 illustrates a feature for germicidal source 22 which may be used to close port 42 of chamber. In particular, FIG. 5 illustrates protrusions 98 jutting out from an upper portion of germicidal source 22. In general, protrusions 98 may come into contact with exterior portions of chamber 24 adjacent to port 42 when germicidal source 22 is drawn into chamber 24 and/or chamber 24 is moved to encase germicidal source 22, effectively closing port 42. In some cases, portions of chamber 24 adjacent to port 42 may include indentations to receive at least an underside of protrusions 98. In other embodiments, however, germicidal source 22 may be void of protrusions 98. In particular, germicidal source 22 may alternatively include a circumferential seal around its upper portion to mate with port 42 as described above. In yet other cases, chamber 24 may include a seal along the circumference of port 42 or chamber 24 may include a door to close port 42 such as described above in reference to FIGS. 4 and 3, respectively. Furthermore, it is noted that protrusions 98 are not exclusive to the configuration of germicidal source 22 depicted in FIG. 5. Rather, protrusions 98 may be included on any configuration of germicidal source 22. Moreover, protrusions need not be limited to the trapezoidal configurations depicted in FIG. 5.

FIG. 5 further illustrates additional germicidal sources 99 within plenum 93. As described in more detail below in reference to FIG. 14, the apparatuses considered herein may, in some embodiments, include program instructions for operating different subsets of germicidal sources for different modes of operation of the apparatuses, specifically whether a disinfection process is being conducted interior to the apparatus or exterior to the apparatus. As such, the apparatuses described herein may, in some embodiments, include multiple germicidal sources. In some cases, the apparatuses described herein may include different types of germicidal sources. In particular, the apparatuses described herein may, in some embodiments, include germicidal sources which differ in the type of germicide they generate (i.e., a liquid, a vapor, a gas, a plasma or germicidal light). In addition or alternatively, the apparatuses described herein may, in some embodiments, include germicidal sources which differ in the manner in which they generate their germicide. For example, the apparatuses described herein may include germicidal discharge lamps and germicidal light emitting diode lamps. In yet other embodiments, the apparatuses described herein may additionally or alternatively include germicidal light sources which differ in the optical properties of the light they generate. For instance, the apparatuses described herein may include xenon discharge lamps and mercury discharge lamps.

It noted that although additional germicidal sources 99 are shown in FIG. 5 along the interior lower sidewalls of circumjacent barrier 92, their location is not necessarily so limited. In particular, they may be located anywhere interior to plenum 93, including any portion of its interior sidewall or along air moving device 94 or a base supporting discharge lamp 90. Moreover, additional germicidal sources 99 are not limited to being smaller than germicidal light source 90 as depicted in FIG. 5. Rather, one or more of additional germicidal sources 99 may be of the same size or larger than germicidal light source 90. Furthermore, additional germicidal sources 99 are not exclusive to the configuration of germicidal source 22 depicted in FIG. 5 or to a germicidal source which has a housing around its source of germicide. In particular, chamber 24 may additionally or alternatively include additional germicidal sources. In further cases, however, apparatus 20 may not include any additional germicidal sources (i.e., apparatus 20 may, in some cases, include a single germicidal source).

Figure 6:
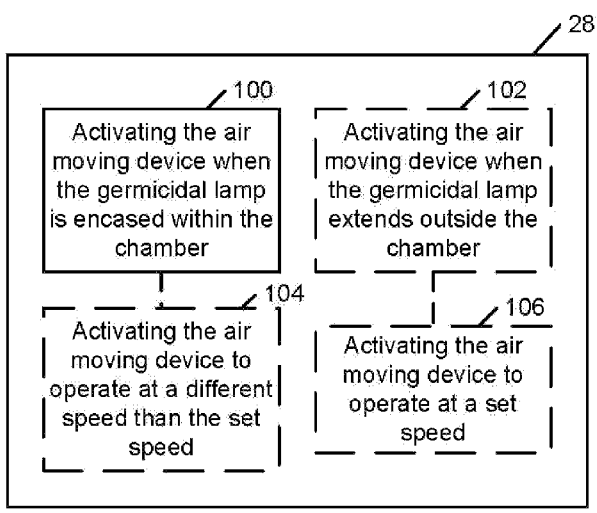
FIG. 6 illustrates example program instructions for activating fans of the apparatuses described herein.

In embodiments in which an air moving device is incorporated within germicidal source 22 and/or chamber 24 (such as described above in reference to FIGS. 4 and 5), program instructions 28 may include code executable by processor 30 for activating the air moving device when germicidal source 22 is encased within chamber 24 as shown by block 100 in FIG. 6. In some cases, particularly but not limited to when germicidal source 22 has an air moving device incorporated therein, program instructions 28 may additionally include code executable by processor 30 for activating the air moving device when germicidal source 22 extends outside of chamber 24 as shown by block 102 in FIG. 6. In some embodiments, program instructions 28 for activating an air moving device when germicidal source 22 extends outside chamber 24 may include the same instructions as activating the air moving device when germicidal source 22 is encased in chamber 24. More specifically, an air moving device may be activated to operate at the same speed when germicidal source 22 extends outside chamber 24 and when germicidal source 22 is encased in chamber 24.

In other cases, program instructions 28 may include different instructions for activating an air moving device in relation to whether germicidal source 22 extends outside chamber 24 or is encased in chamber 24. For example, program instructions 28 may, in some embodiments, include code executable by processor 30 for activating an air moving device to respectively operate at different speeds when germicidal source 22 is encased with chamber 24 and when germicidal source 22 is not encased with chamber 24 as respectively denoted in blocks 104 and 106 of FIG. 6. In particular embodiments, program instructions 28 may include code executable by processor 30 for activating an air moving device to operate at a higher speed when germicidal source 22 is encased with chamber 24 than when germicidal source 22 is not encased with chamber 24. In particular, air disinfection processes conducted within chamber 24 do not have the added benefit of disinfecting ambient air of apparatus 20 (i.e., air not drawn into apparatus 20) as is done when germicidal source 22 extends exterior to chamber 24 (i.e., through the transmission of germicide exterior to apparatus 20). Thus, it may be advantageous to increase the air moving device speed when germicidal source 22 is encased within chamber 24.

As noted above, air outlet 96 of germicidal source 22 depicted in FIG. 5 may, in some embodiments, include an ozone reducing device and, in some cases, further include an air flow regulator to respectively route air through a first passageway comprising the ozone reducing device and a second passage way not including the ozone reducing device. In general, the second passageway is either void of an ozone reducing device or comprises an ozone reducing device having substantially less efficacy than the ozone reducing device in the first passageway. It is noted that in some alternative embodiments, a door covering port 42 of chamber 24 (such as door 76 depicted in FIG. 3) may similarly include a portion with an ozone reducing device and portion without the ozone reducing device and, in some cases, an air flow regulator. In particular, in cases in which germicidal source 22 includes a UV light source, ozone produced from the lamp may not be filtered when germicidal source 22 extends exterior to the chamber and when apparatus 20 is operated within a vacated room/area. On the contrary, when apparatus 20 is operated in an occupied room with germicidal source 22 encased in chamber 22, ozone produced from the UV light may be reduced due to regulatory exposure limits and/or concerns of exposure by individuals occupying a room. As such, it may be just as viable for a door covering port 42 to include ozone reducing device and, in some cases, an air flow regulator instead of or in addition to germicidal source 22 including such components.

In any case, an air flow regulator for respectively routing air through an ozone reducing device and not through the ozone reducing device may generally be activated/operated depending on operating parameters and/or modes of disinfection processes employed by apparatus 20. For instance, program instructions 28 may, in some embodiments, include code executable by processor 30 for controlling an air flow regulator such that air is routed through a first passageway comprising an ozone reducing device when the germicidal lamp is encased in the chamber and air is routed through a second passageway not including the ozone reducing device when the germicidal lamp extends outside the chamber as respectively shown by blocks 110 and 112 in FIG. 7. In addition or alternatively, program instructions 28 may include code executable by processor 30 for controlling an air flow regulator such that air is routed through the second passageway not including the ozone reducing device during a first portion of a disinfection process and air is routed to through the first passageway including the ozone reducing device during a second portion of the disinfection process as respectively shown by blocks 114 and 116 in FIG. 7.

In general, controlling the air flow regulator in the latter manner allows ozone to be generated at a relatively high level (e.g., a level which offers increased deodorizing and disinfection effects) during a first portion of the disinfection cycle and then reduces ozone generation during a finishing portion of the disinfection cycle such that the ozone concentration in a room/area being disinfected is below a set value (e.g., the OSHA PEL/TLV limit). Such code may be particularly suitable for operations of apparatus 20 in an area/room which has been vacated, but it may be used in occupied areas and room as well, particularly if the higher levels of generated ozone are not harmful to occupants. In any case, the code may be activated when germicidal source 22 extends outside of chamber 24 or when it is encased within chamber 24 (i.e., when apparatus 20 is operated to conduct a disinfection process exterior or interior to chamber 24).

Figure 7:
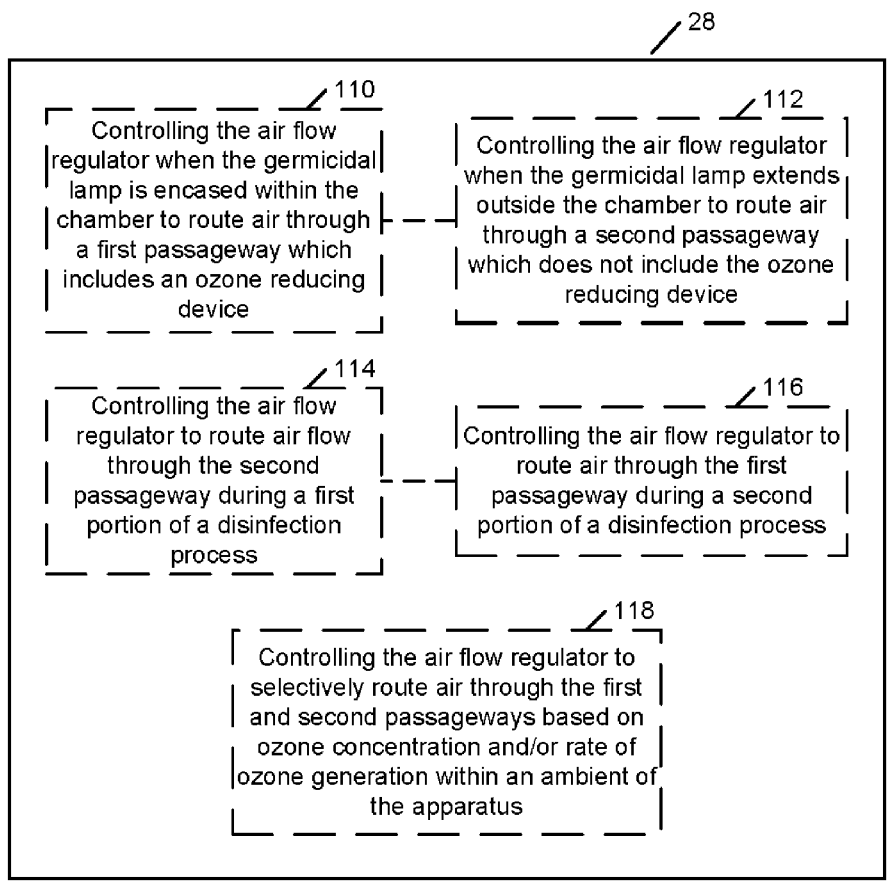
FIG. 7 illustrates example program instructions for controlling air flow regulators of the apparatuses described herein.

In some embodiments, program instructions 28 may include code for controlling an air flow regulator based on the ozone concentration and/or the rate of ozone generation in a room/area as shown by block 118 in FIG. 7. In particular, program instructions 28 may, in some cases, include code for receiving information regarding ozone concentration and/or the rate of ozone generation in a room/area from a sensor in the room/area and, in response, controlling an air flow regulator such that air is routed through a first passageway comprising an ozone reducing device when level of ozone concentration or ozone generation is greater than a predetermined threshold and air is routed through a second passageway not including the ozone reducing device when a level of ozone concentration or ozone generation is less than the same or a different predetermined threshold. In some cases, control of the air flow regulator may be further based on a run time set for a disinfection process, specifically determining when to reduce ozone during a room/area disinfection process such that the concentration of ozone in the room/area at a designated time (e.g., the end of the disinfection cycle or a set time after the end of the disinfection cycle) will be below a set value. In this manner, the benefits of ozone generation may be increased/optimized for a given room.

In some cases, the sensor/s used to analyze the ozone concentration/rate of generation may be attached to apparatus 20. In other cases, however, the sensor/s may be positioned apart from apparatus 20, particularly a set distance from the apparatus to obtain information more representative of the ozone concentration/rate of generation in the room/area. An additional optional feature is to have the sensor/s monitor ozone degradation and program instructions 28 determine based on degradation information from the sensor/s whether a concentration of ozone in the room/area will be below a set value at a designated time and, optionally, if it will not, controlling the air flow regulator to route air through the ozone reducing device prior to a previously determined time to get the concentration of zone in the room/area at the designated time below the set value.

Figure 8:
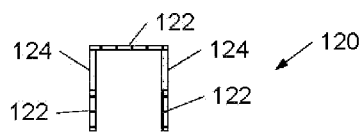
FIG. 8 illustrates an example air flow regulator which may be used in the apparatuses described herein.
Figure 9A:
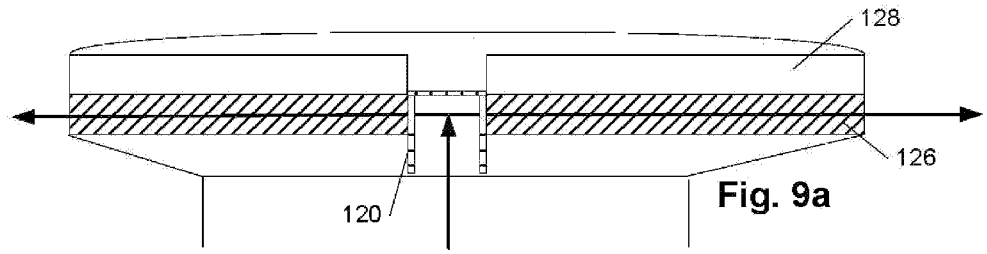
FIGS. 9a and 9b illustrate example positions of the air flow regulator depicted in FIG. 8 relative to an air outlet of an apparatus.
Figure 9B:
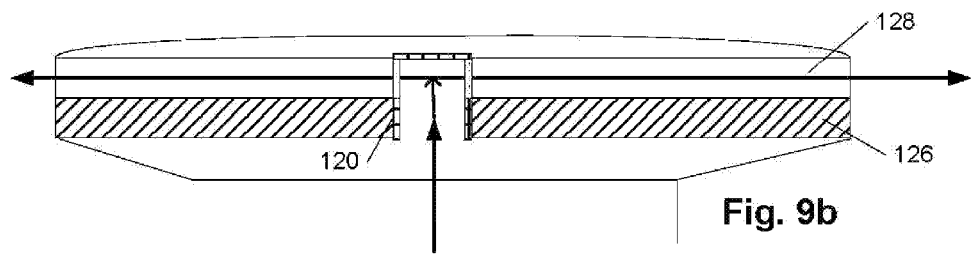
Figure 10:
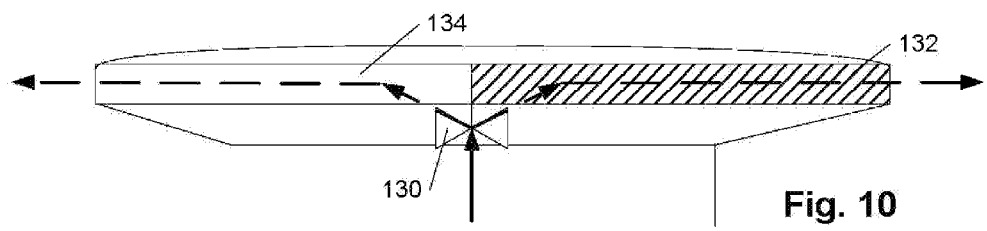
FIG. 10 illustrates another configuration of an air flow regulator which may be used in the apparatuses described herein.

Examples of air flow regulators which may be used in the apparatuses described herein are shown in FIGS. 8-10. It is noted that other air flow regulators may be considered for the apparatuses described herein and, thus, options for air flow regulators should not be limited to the depictions in the drawings. Furthermore, the configurations of passageways to which air flow regulators selectively route air may vary among apparatuses and may be different from those depicted in FIGS. 9a-10. For example, the apparatuses described herein could include a bypass line around an ozone reducing device (or a passageway comprising an ozone reducing device). Other configurations can be considered as well. FIG. 8 shows air flow regulator 120 including a top member of air blocking material 122 and two side members extending downward from the ends of the top member each having an upper portion of air permeable material 124 and a lower portion of air blocking material 122. An alternative configuration would be to have air flow regulator 120 include a bottom member of air permeable material connecting the bottom ends of its side portions, in addition or instead of having a top member of air blocking material. In general, air blocking material 122 may include any material sufficient to block the passage of air therethrough and air permeating material 124 may include any configuration which allows passage of air therethrough, such as a mesh or a permeated structure. It is noted that the portions of air blocking material 122 and air permeable material 124 need not be equal on a given side member of air flow regulator 120 as depicted in FIG. 8. Furthermore, the air blocking material of the side members of air flow regulator 120 need not be the same as the air blocking material of the top member.

In any case, to regulate air flow in the apparatuses described herein, air flow regulator 120 is moved up and down to align air permeable material 124 of its side members with an ozone reducing device (or a passageway including an ozone reducing device) and a passageway which does not include the ozone reducing device. FIGS. 9a and 9b illustrate such an operation of air flow regulator 120 in an example configuration of an apparatus having an ozone reducing device. In particular, FIG. 9a illustrates a cross-sectional view of a portion of apparatus 20 (e.g., in an upper portion of germicidal source 22 or in a door covering port 42 of chamber 24) having air flow regulator 120 disposed therein such that air permeable material 124 of its side members is aligned with ozone reducing device 126 (or a passageway including ozone reducing device 126). In addition, FIG. 9a illustrates air blocking material 122 of the side members of air flow regulator 120 aligned with passageway 128 which does not include ozone reducing device 126. With such an arrangement and placement of air flow regulator 120, air flow is directed through ozone reducing device 126 as denoted by the doubled arrow line.

Upon activation of an actuator coupled to air flow regulator 120 (such as in response to activation of the actuator by program instructions 28 for any of the scenarios described in reference to blocks 112, 114, and 118 in FIG. 7), air flow regulator 120 is moved such that air permeable material 124 along its side members is aligned with passageway 128 as shown in FIG. 9b. In addition, air blocking material 122 of the side members of air flow regulator 120 is aligned with ozone reducing device 126 (or a passageway including ozone reducing device 126). As a result, air flow through the apparatus bypasses ozone reducing device 126, as denoted by the doubled arrow line in FIG. 9b, and a higher concentration of ozone is emitted into the ambient of the apparatus. In particular, the passageway 128 is either void of an ozone reducing device or comprises an ozone reducing device having substantially less efficacy than ozone reducing device 126. In some of the apparatuses described herein, an actuator coupled to air flow regulator 120 may be activated to have air permeable material 124 partially aligned with both ozone reducing device 126 (or a passageway including ozone reducing device 126) and passageway 128 to offer further control of ozone concentration emitted from the apparatus. In some cases, program instructions 28 or an actuator coupled to air flow regulator 120 may be configured to regulate a percentage to which air permeable material 124 may be aligned with either of ozone reducing device 126 (or a passageway including ozone reducing device 126) and passageway 128.

In any case, it is noted that the placement of ozone reducing device 126 (or a passageway including ozone reducing device 126) and passageway 128 may be reversed (i.e., ozone reducing device 126 (or a passageway including ozone reducing device 126) may alternatively be disposed above passageway 128). In embodiments in which a carbon filter is used as an ozone reducing device in conjunction with air flow regulator 120 and a surface of the carbon filter borders passageway 128, an additional optional feature is to have the border of the carbon filter coated with a material which prevents ozone passing through passageway 128 from interacting with the filter. In embodiments in which a carbon filter is considered for an ozone reducing device for the apparatuses described herein, an advantage of the configuration of air flow regulator 120 relative to air flow regulator valve 130 described below in reference to FIG. 10 is that the configuration of air flow regulator 120 enables a larger carbon filter to be used, potentially increasing the life of the carbon filter.

Another air flow regulator which may be considered for the apparatuses described herein is depicted in FIG. 10. In particular, FIG. 10 illustrates air flow regulator valve 130 positioned at an intersection of routing air through ozone reducing device 132 (or a passageway including ozone reducing device 132) and routing air through passageway 134 which does not include ozone reducing device 132. In general, the passageway 134 is either void of an ozone reducing device or comprises an ozone reducing device having substantially less efficacy than ozone reducing device 132. Air flow regulator 130 may be configured such that all air may be routed through ozone reducing device 132 (or a passageway including ozone reducing device 132) or through passageway 134 at a given time. In further embodiments, air flow regulator 130 may, in some cases, be configured to route air through both ozone reducing device 132 (or a passageway including ozone reducing device 132) and passageway 134 at given time. In some of such cases, air flow regulator 130 may be configured to regulate a percentage of air routed through reducing device 132 (or a passageway including ozone reducing device 123) and/or passageway 134 to offer further control of ozone concentration emitted from the apparatus.

As noted above, the apparatuses presented herein include configurations for conducting different disinfection modes exterior and interior to the apparatus, particularly room/area disinfection processes exterior to the apparatus and object and/or air disinfection processes interior to the apparatus. A commonality among the apparatuses is that they include a moveable germicidal source and/or a moveable shield and program instructions for activating power supply circuitry to operate the germicidal source. A number of different configurations may be considered with such features, particularly for achieving the noted objective of being able to conduct disinfection processes interior and exterior to the apparatus. As such, the apparatuses described herein are not restricted to the configuration of apparatus 20 in FIG. 1. As described in more detail below, FIGS. 11-13 illustrate some alternative configurations of apparatuses configured for conducting different disinfection processes interior and exterior to the apparatuses. However, as with apparatus 20 described in reference to FIG. 1, the apparatuses described in reference to FIGS. 11-13 are examples and several other configurations may be considered. For example, a compilation of different features from the apparatuses described in reference to FIGS. 1 and 11-13 may be considered.

A notable difference between the apparatuses described in reference to FIGS. 11-13 and apparatus 20 described in reference to FIG. 1 is that the shields of the apparatuses of FIGS. 11-13 are not chambers. Rather, the apparatuses of FIGS. 11-13 include shields which are configured with other features of the apparatuses to form chambers to encase the germicidal source/s of the apparatuses. Alternatively stated, the apparatuses of FIGS. 11-13 include shields which may be brought in proximity to germicidal source/s of the apparatuses (and/or the germicidal source/s may be brought in proximity to the shields) such that germicide projected from the germicidal source/s is substantially contained in the apparatus. In addition, the shields and/or the germicidal source/s of FIGS. 11-13 may be brought out of proximity with each other such that germicide projected from the germicidal source/s is projected exterior to the apparatus. Alternatively stated, the apparatuses of FIGS. 11-13 include moveable shields and/or germicidal source/s such that the germicidal source/s may be exposed to an ambient of the apparatus, in affect disassembling the chamber formed by the shields and other features of the apparatuses when the germicidal sources are encased.

In any case, the apparatuses described in reference to FIGS. 11-13 may include any of the features described in reference to apparatus 20 of FIG. 1. In particular, the apparatuses described in reference to FIGS. 11-13 and any variations thereof may include power circuitry 26, program instructions 28, processor 30, user interface 32, remote user interface 34, base 36, sensor/s 38, sensor/s 48, support members 40, ports 42 and 70, doors 72 and 76, shelves 74, baskets, air moving devices 80 and 94, air inlets, air outlets 82, seal 84, circumjacent barrier 92, ozone reducing device 96, protrusions 98, additional germicidal sources 99, air flow regulator devices 120 and 130, and any variations thereof discussed in reference to apparatus 20 of FIG. 1. Such features are not shown in the apparatuses of FIGS. 11-13 to simplify the drawings. Furthermore, such features are not described in reference to FIGS. 11-13 for the sake of brevity. Moreover, the apparatuses described in reference to FIGS. 11-13 and any variations thereof may include any of the specific program instructions described in reference to FIGS. 2, 6 and 7 as well as any variations thereof described in reference to FIGS. 2, 6, and 7. The specific program instructions have not been reiterated for the apparatuses of FIGS. 11-13 for the sake of brevity. Yet further optional features for the apparatuses described in reference to FIGS. 11-13 and any variations thereof include wheels (motorized or not motorized) and/or a handle to affect portability for the apparatus.

Turning to FIG. 11, apparatus 140 is shown including germicidal sources 142 arranged in frame 144 with shield 146 retracted. In some cases, the backside of apparatus 140 may include a shield coupled to frame 144 similar to shield 146. In other embodiments, the backside of apparatus 140 may include a backside panel spanning the areal dimension of frame 144 to prevent emission of germicide from the backside of apparatus 140. In any case, apparatus 140 may be mountable on a wall or a ceiling. Alternatively, apparatus 140 may be a standalone device. In general, shield 146 is moveable within apparatus 140, particularly to enclose germicidal sources 142 within frame 144 for disinfection processes conducted interior to frame 144 and further to expose germicidal sources 142 to an ambient of apparatus 140 for disinfection processes conducted exterior to frame 144. As shown in FIG. 11, shield 146 may, in some embodiments, be a roller shade or have some other retractable configuration, such as an accordion configuration or a nested configuration. In such cases, shield 146 may move along tracks within frame 144 traversing the length of the window exposing germicidal sources 142 such that shield 146 may enclose germicidal sources 142 when closed. In other embodiments, shield 146 may include one or more hinged doors, sliding doors or clamp-on removable covers. In any case, shield 146 may be manually actuated and/or apparatus 140 may include an actuator to automate movement of shield 146.

It is noted that apparatus 140 is not restricted to the placement of shield 146 shown in FIG. 11. In particular, shield 146 may be supported adjacent any edge of frame 144 and extend to an opposing edge of the frame, including the top and bottom edges of frame 144. Moreover, the dimensions and shape of frame 144 may vary from that depicted in FIG. 11. More specifically, frame 144 is not limited to being rectangular and/or having the relatively thin sidewalls depicted in FIG. 11. Furthermore, the orientation of apparatus 140 is not limited to its longitudinal dimension being horizontal. Moreover, apparatus 140 is not limited to having multiple cylindrical germicidal sources orientated in the manner shown in FIG. 11. Rather, apparatus 140 may include any number, size, shape and orientation of germicidal sources. Moreover, germicidal sources 142 may include the same type of germicidal source or different types of germicidal sources. In some cases, apparatus 140 may be configured to move one or more of germicidal sources 142 to extend out of frame 144 to enhance distribution of germicide/s generated therefrom into an ambient of the apparatus. An example configuration to offer such an option may include retractable tracks extending out from frame 144 in alignment with germicidal sources 142, along which the germicidal sources may be moved manually or by an actuator.

Furthermore, as noted above, apparatus 140 may include any of the features described in reference to apparatus 20 of FIG. 1, including but not limited to air moving devices, air inlets, air outlets, baskets and/or shelves. In general, air moving device/s, air inlet/s, and air outlet/s may be arranged within any side of frame 144 and/or shield 146. In addition or alternatively, air moving device/s may be arranged internal to frame 144, particularly but not necessarily in alignment with air inlet/s or air outlet/s within the frame. In any case, air moving device/s may be arranged upstream or downstream of an air stream induced through frame 144 when closed. In some cases, apparatus 140 may include an air moving device disposed at one end of at least one of germicidal sources 142 (and, in some cases, include an air moving device disposed at the end of each of germicidal sources 142) to induce an air stream which flows substantially parallel with the longitudinal dimension of the germicidal sources, such as described for germicidal source 90 in reference to FIG. 5. In other cases, apparatus 140 may have air moving devices arranged to induce an air stream that transverses germicidal sources 142.

FIG. 12 illustrates a similar disinfection apparatus to apparatus 140, but differs by the inclusion of a hinge between two sections of framed germicidal sources instead a shield door. In particular, FIG. 12 illustrates apparatus 150 having germicidal sources 152 arranged in framed sections 154 joined by hinge 156. In general, each of framed sections 154 includes a backside panel spanning the areal dimension of the respective section to prevent emission of germicide from the backside of apparatus 150. In some cases, one or both of framed sections 154 may be mountable on a wall or a ceiling. Alternatively, apparatus 150 may be a standalone device. In any case, one or both of framed sections 154 are pivotal about hinge 156 such that forefront edges 158 of framed sections 154 may be brought into contact with each other to enclose germicidal sources 152 for disinfection processes conducted interior to apparatus 150 and further that they may be disengaged to expose germicidal sources 152 to an ambient of apparatus 150 for disinfection processes conducted exterior to frame sections 154. In this manner, one or both of framed sections 154 function as moveable shields within apparatus 150 to form a chamber about germicidal sources 152.

In general, framed sections 154 may be configured to pivot any degree of rotation about hinge 156, depending on the design specifications of apparatus 150. For instance, in some cases, one or both of framed sections 154 may be configured such that forefront edges 158 are at a maximum 180 degrees relative to each other (i.e., framed sections 154 are oriented in a line). In other cases, one or both of framed sections 154 may be configured such that backside panels of framed sections 154 come into contact with each other. In any case, the inclusion of hinge 156 within apparatus 150 may desirably offer a manner in which to selectively direct germicide within a room/area for disinfection processes conducted exterior to apparatus 150. One or both of framed sections 154 may be manually actuated and/or apparatus 150 may include one or more actuators to automate movement of one or both of framed sections 154.

Similar to frame 144 of apparatus 140 described in reference to FIG. 11, the dimensions and shape of framed sections 154 may vary from that depicted in FIG. 12. More specifically, framed sections 154 are not limited to being rectangular and/or having the relatively thin sidewalls depicted in FIG. 12. Furthermore, the orientation of apparatus 150 is not limited to framed sections 154 being horizontal displaced from each other (e.g., one of framed sections 154 may be arranged above the other with hinge 154 arranged substantially horizontally). Moreover, apparatus 150 is not limited to having multiple cylindrical germicidal sources in each of framed sections 154 orientated in the manner shown in FIG. 12. Rather, apparatus 150 may include any number, size, shape and orientation of germicidal sources within each of framed sections 154. Moreover, germicidal sources 152 may include the same type of germicidal source or different types of germicidal sources in one or both of framed sections 154. Similar to apparatus 140 described in reference to FIG. 11, apparatus 150 may be configured to move one or more of germicidal sources 152 to extend out of framed sections 154 to enhance distribution of germicide/s generated therefrom into an ambient of the apparatus. An example configuration to offer such an option may include retractable tracks extending out from framed sections 154 in alignment with germicidal sources 152, along which the germicidal sources may move.

Furthermore, as noted above, apparatus 150 may include any of the features described in reference to apparatus 20 of FIG. 1, including but not limited to air moving devices, air inlets, air outlets, baskets and/or shelves. In general, air moving device/s, air inlet/s, and air outlet/s may be arranged within any side of framed sections 154. In addition or alternatively, air moving device/s may be arranged internal to framed sections 154, particularly but not necessarily in alignment with air inlet/s or air outlet/s within the frames. Similar to apparatus 140 described in reference to FIG. 11, air moving device/s may be arranged upstream or downstream of an air stream induced through framed sections 154 when closed. In some cases, apparatus 150 may include an air moving device disposed at one end of at least one of germicidal sources 152 (and, in some cases, an air moving device disposed at the ends of each of germicidal sources 152) to induce an air stream which flows substantially parallel with the longitudinal dimension of the germicidal sources, such as described for germicidal source 90 in reference to FIG. 5. In other cases, apparatus 150 may have air moving devices arranged to induce an air stream that transverses germicidal sources 152.

FIG. 13 illustrates yet another configuration of an apparatus for conducting different disinfection modes exterior and interior to the apparatus, particularly room/area disinfection processes exterior to the apparatus and object and/or air disinfection processes interior to the apparatus. In particular, FIG. 13 illustrates apparatus 160 having germicidal sources 162 arranged around reflector 164 between upper base 166 and lower base 168. In addition, apparatus 160 includes shield 169 which is configured to attach to upper base 166 and/or lower base 168 and wrap around germicidal sources 162 to enclose germicidal sources 162 for disinfection processes conducted interior to apparatus 160. On the contrary, detachment of shield 169 from upper base 166 and/or lower base 168 exposes germicidal sources 162 to an ambient of apparatus 160 for disinfection processes conducted exterior to apparatus 160. Although not shown, shield 169 may include any type and any number of fasteners for closing the open ends of the shield around germicidal sources 162 as well as attaching shield 169 to upper base 166 and lower base 168. In some cases, the fastener/s may have quick release configurations to aid a user in connecting and disconnecting them easily and quickly. In some embodiments, shield 169 may be made of a relatively lightweight material for ease of mounting the shield on upper base 166 and lower base 168. In addition, shield 168 may, in some cases, include a sturdy, but relatively pliable material and/or may include multiple sections which are joined with bendable interfaces to aid in wrapping the shield around germicidal sources 162.

It is noted that shield 169 may include any shape, specifically shield 169 may include any polygonal shape or shield 169 may be circular. In addition, shield 169 may include any number of individual sections coupled together rather than be a single contiguous piece as depicted in FIG. 13. Furthermore, shield 169 need not be completely removable from upper base 166 and/or lower base 168. Rather, shield 169 may be fixedly attached at one or more locations on upper base 166 and/or lower base 168 and may be foldable and/or retractable in itself to minimize the area it occupies when it is not surrounding germicidal lamps 162. For example, shield 169 may be a roller shade or have some other retractable configuration, such as an accordion configuration or a nested configuration. In any case, the dimensions and shape of the components comprising apparatus 160 may vary from that depicted in FIG. 13. For example, apparatus 160 is not limited to having multiple cylindrical germicidal sources orientated in the manner shown in FIG. 13. Rather, apparatus 160 may include any number, size, shape and orientation of germicidal sources. In cases in which apparatus 160 includes multiple germicidal sources, germicidal sources 162 may include the same type of germicidal source or different types of germicidal sources. In addition, reflector 164, upper base 166 and lower base 168 are not limited to the configuration and relative dimensions depicted in FIG. 13. For example, reflector 164 need not have an hour glass shape and, in some cases, reflector 164 may be omitted from apparatus 160. Further yet, apparatus 160 is not limited to having wheels coupled to the bottom of lower base 168. In particular, apparatus 160 may alternatively by a stationary device.

Furthermore, as noted above, apparatus 160 may include any of the features described in reference to apparatus 20 of FIG. 1, including but not limited to air moving devices, air inlets, air outlets, baskets and/or shelves. In general, air moving device/s, air inlet/s, and air outlet/s may be arranged within shield 169, upper base 166 and/or lower base 168. In addition or alternatively, air moving device/s may be arranged within reflector 164 or on a surface of reflector 164, shield 169, upper base 166 and/or lower base 168. In any case, air moving device/s may be arranged upstream or downstream of an air stream induced through shield 169 when closed. In some cases, apparatus 160 may include an air moving device disposed at one end of at least one of germicidal sources 162 (and, in some cases, an air moving device disposed at ends of each of germicidal sources 162) to induce an air stream which flows substantially parallel with the longitudinal dimension of the germicidal sources, such as described for germicidal source 90 in reference to FIG. 5. In other cases, apparatus 160 may have air moving devices arranged to induce an air stream that transverses germicidal sources 162.

Several examples of program instructions 28 for operating components of the apparatuses presented herein are described in reference to FIGS. 2, 6 and 7. Additional or alternative program instructions, particularly flows of program instructions, which may be considered for any of the apparatuses considered herein (i.e., apparatuses having configurations for conducting interior and exterior disinfection processes) are shown in flowcharts in FIGS. 14-17. It is noted that the processes described in reference to FIGS. 14-17 are not necessarily mutually exclusive to the flow of program instructions depicted in those figures. Furthermore, any of the program instructions described in reference to FIGS. 2, 6 and 7 may be used in conjunction with each other or any of the program instructions included in the flowcharts of FIGS. 14-17.

Figure 14:
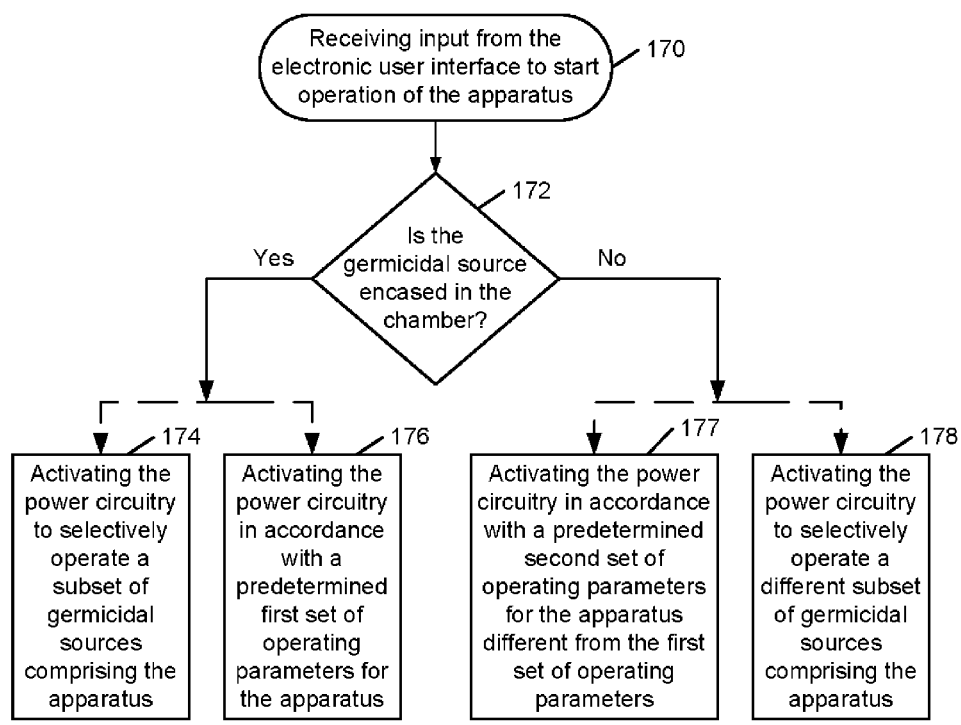
FIGS. 14-17 illustrate flowcharts of example processes which may be conducted in conjunction with the apparatuses described herein.

FIG. 14 illustrates a flowchart including block 170 at which input is received from an electronic user interface to start operation of a disinfection apparatus. Upon receipt of such input a determination is made at block 172 as to whether a germicidal source is encased in a chamber of the apparatus. Alternatively, a determination may be made as to whether the germicidal source is exterior to the chamber (and/or whether the germicidal source is arranged in proximity of a shield of the apparatus). In either case, upon an affirmative determination at block 172, the power circuitry of the apparatuses may be activated in one or two manners as denoted in blocks 174 and 176. Furthermore, upon determining the condition at block 172 is not true, the power circuitry of the apparatuses may be activated in one or two manners as denoted in blocks 178 and 177, each of which respectively differ but yet correlate to the instructions set forth in blocks 174 and 176.

In particular, in embodiments in which the apparatus includes multiple disinfection sources, the power circuitry of the apparatus may be activated, upon an affirmative determination at block 172, to selectively operate a subset of the disinfection sources for a disinfection process as denoted in block 174. Conversely, upon determining the condition set forth in block 172 is not true, the power circuitry of the same apparatus may be activated to selectively operate a different subset of the disinfection sources for a disinfection process as denoted in block 178. In some cases, the subset of the multiple germicidal sources activated in block 174 may include at least one germicidal source that generates a different germicide than at least one of the germicidal sources of the subset activated in block 178. In additional or alternative embodiments, the subset of the germicidal sources activated in block 174 may include at least one germicidal source that generates its germicide in a manner different than at least one of the germicidal sources of the subset activated in block 178. For example, the subset of the germicidal sources activated in block 174 may include light emitting diode lamp/s and the subset of germicidal sources activated in block 178 may include discharge lamp/s or vice versa.

In yet other embodiments in which the subsets of germicidal sources activated for the processes depicted in blocks 174 and 178 each include germicidal lamps, the germicidal lamps may differ in the optical properties of the light they generate. For instance, the subset of the germicidal sources activated in block 174 may include mercury discharge lamp/s and the subset of germicidal sources activated in block 178 may include xenon discharge lamp/s or vice versa. Other variances between one or more of the germicidal sources of the different subsets may be considered as well, such as but not limited to size, shape and intensity of germicidal dispersal. In any case, regardless of the type of variance between the germicidal sources of the different subsets activated with respect to blocks 174 and 178, in some embodiments, each germicidal source of the one subset may differ from all of the germicidal sources of the other subset. In yet other cases, the type and configuration of germicidal sources of the different subsets may not vary. In any case, the term subset as used herein refers to any number of elements (i.e., one or more) of a group which is less than all elements of the group.

Another option for activating power circuitry of an apparatus upon determination of the relative location of a germicidal lamp within the apparatus at block 172 is to activate the power circuitry in accordance with different operating parameters for the apparatus as set forth in blocks 176 and 177. In particular, upon an affirmative determination at block 172, the power circuitry of an apparatus may be activated in accordance with a predetermined set of operating parameters for the apparatus as denoted in block 176. In addition, upon determining the condition set forth in block 172 is not true, the power circuitry of the same apparatus may be activated in accordance with a different predetermined set of operating parameters for the apparatus as denoted in block 177. Such processes may be conducted in addition or alternative to the processes set forth in blocks 174 and 178. Furthermore, the processes of blocks 176 and 177 may be conducted in apparatuses having a single germicidal source or multiple germicidal sources.

In any case, the different sets of predetermined operating parameters referenced in blocks 176 and 177 may include any number of different operating parameters and may include any of the variances of operating parameters described above in reference to FIGS. 2, 6 and 7, including but not limited to applying different amounts of power to the germicidal source/s, applying power to the germicidal source's for different durations, applying trigger voltages at different frequencies, activating a fan to operate a different speeds, and controlling an air flow regulator to route air through different passageways. In yet other embodiments, one of the sets of operating parameters may include a parameter for a particular variable (such as but not limited to fan speed) and the other set of operating parameters may be void of instructions for that variable. Such a scenario may be advantageous when a component is used for a particular disinfection mode, but is not used for other disinfection modes.

Figure 15:
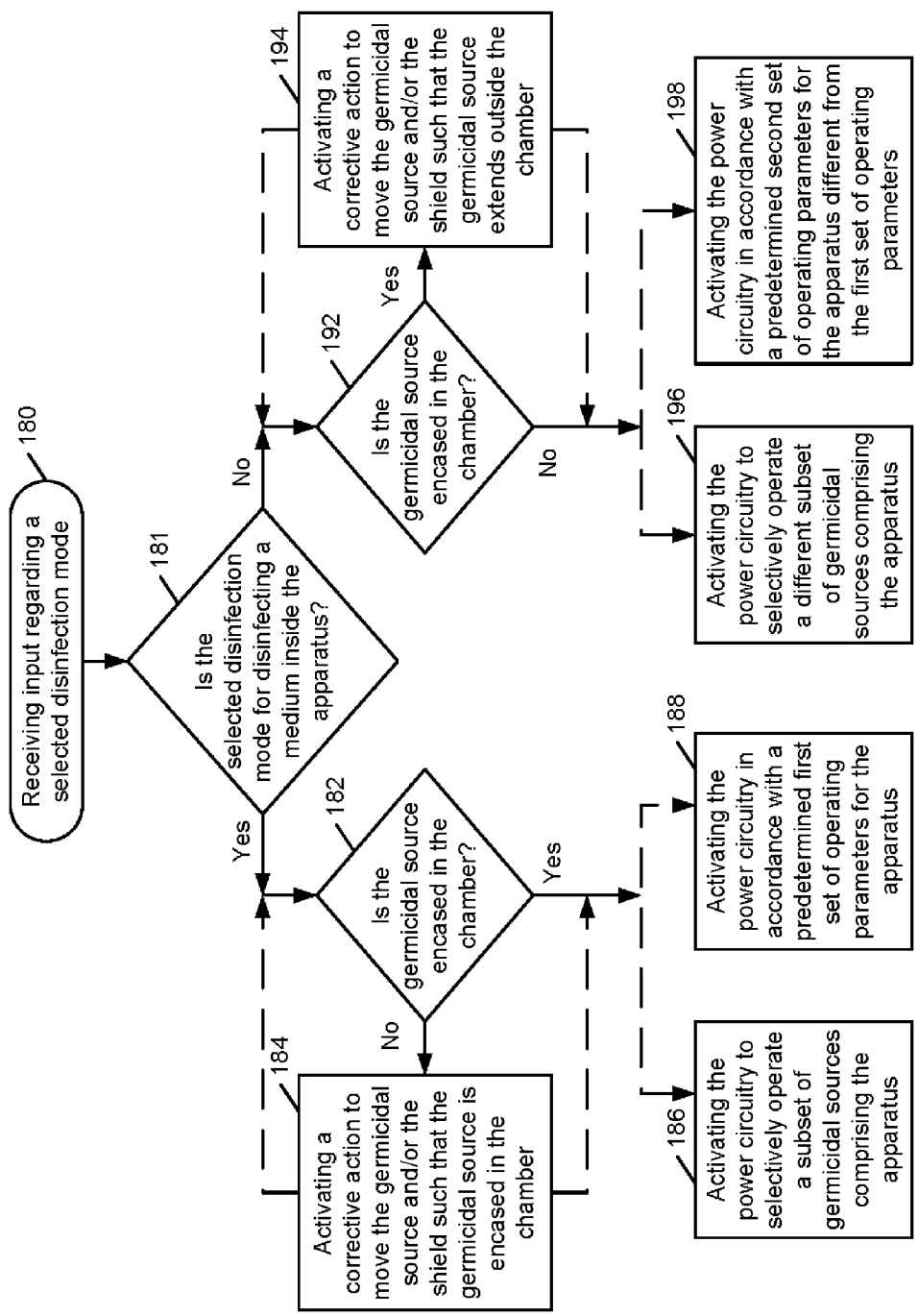

Turning to FIG. 15, another flowchart is shown of processes that may be performed by any of the apparatuses described herein. In particular, FIG. 15 shows block 180 at which input is received regarding a selected disinfection mode, particularly from a user interface of a disinfection apparatus. In general, the input may be indicative of either of a disinfection mode for primarily disinfecting a medium inside the apparatus or a disinfection mode for primarily disinfecting a medium exterior to the apparatus. In some embodiments, the input may be more specific to the medium to be disinfected. For example, the input may be indicative of either a disinfection mode for primarily disinfecting air interior to the apparatus or a disinfection mode for primarily disinfecting a room/area. In other embodiments, the input may be indicative of either a disinfection mode for primarily disinfecting objects interior to the apparatus or a disinfection mode for primarily disinfecting a room/area. In yet other embodiments, the input may be indicative of a disinfection mode selected from more than two disinfection modes. For instance, the input may be indicative of a disinfection mode for primarily disinfecting air interior to the apparatus, a disinfection mode for primarily disinfection objects interior to the apparatus, or a disinfection mode for primarily disinfecting a room/area. In any case, the user interface of the disinfection apparatus may include any number and type of input controls to allow selection of the different disinfection modes offered by an apparatus. For example, the input controls may be touch contacts (e.g., buttons or touch screen activated pads) or may be audio controlled. Furthermore, the options of the different modes offered by an apparatus may be displayed to a user in any manner known in the art, including but not necessarily limited to alphanumerical characters, numerals and/or pictures.

In some embodiments, upon receiving the input regarding the selected disinfection mode, a determination is made as to whether the selected disinfection mode is for primarily disinfecting a medium inside the apparatus as shown by block 181. In other embodiments, a determination may be made as to whether the selected disinfection mode is for primarily disinfecting a medium outside the apparatus. In such latter cases, it would be apparent to one skilled in the art that the processes following an affirmative determination and a determination which is not true would be reversed relative to what is shown in FIG. 15. In yet other cases, the process of block 181 may be omitted and input regarding selected disinfection modes for primarily disinfecting a medium inside and outside the apparatus may automatically continue to blocks 182 and 192, respectively. In any case, at blocks 182 and 192, a determination is made as to whether a germicidal source of the apparatus is encased in a chamber of the apparatus. Alternatively, a determination may be made as to whether the germicidal source is exposed to an ambient of the apparatus. In such latter cases, it would be apparent to one skilled in the art that the processes following an affirmative determination and a determination which is not true would be reversed relative to what is shown in FIG. 15.

As shown in FIG. 15, if a determination is made at block 182 that the germicidal source is not encased within a chamber of the apparatus, a correction action may be activated to move the germicidal source and/or a shield of the apparatus such that the germicidal source is encased in a chamber of the apparatus as denoted in block 184. In some embodiments, the corrective action may be a notification to a user of the apparatus to move the appropriate component (such as via the user interface on the apparatus or via the remote user interface). The notification may be in any form known in the art, including a visual display or an audible sound/instruction. In other embodiments, the corrective action may be automated movement of the germicidal source and/or the shield to form a chamber with the germicidal source therein. In such cases, the corrective action may be to activate actuator/s coupled to the germicidal source and/or the shield to affect their movement.

In any case, upon the germicidal source and/or the shield being moved to form a chamber in which the germicidal source is encased (via automated movement or via manual movement with receipt of a confirmation signal that the component/s were moved), one or two of the processes denoted in blocks 186 and 188 may be conducted. The processes denoted in blocks 186 and 188 are the same processes denoted in blocks 174 and 176 of FIG. 14. The description of such processes in reference to FIG. 14 is referenced for blocks 186 and 188 and is not reiterated for the sake of brevity. In some cases, for assurance purposes, a determination may be made as to whether the germicidal source is encased in the chamber at block 182 after the germicidal source and/or the shield has been moved to form a chamber in reference to the corrective action activated in block 184. In such cases, upon an affirmative determination at block 182, one or both of the process denoted in blocks 186 and 188 may be conducted.

Turning to block 192, if a determination is made that the germicidal source is encased within a chamber of the apparatus, a correction action may be activated to move the germicidal source and/or a shield of the apparatus such that the germicidal source is exposed to an ambient of the apparatus as denoted in block 194. Similar to the corrective action discussed in reference to block 184, the corrective action may a notification to a user of the apparatus to move the appropriate component (such as via the user interface on the apparatus or via the remote user interface). In other embodiments, the corrective action may be automated movement of the germicidal source and/or the shield to form a chamber with the germicidal source therein. In any case, upon the germicidal source and/or the shield being moved to such that the germicidal source is exposed to an ambient of the apparatus (via automated movement or via manual movement with receipt of a confirmation signal that the component/s were moved), one or two of the processes denoted in blocks 196 and 198 may be conducted. The processes denoted in blocks 196 and 198 are the same processes denoted in blocks 177 and 178 of FIG. 14. The description of such processes in reference to FIG. 14 is referenced for blocks 196 and 198 and is not reiterated for the sake of brevity. In some cases, for assurance purposes, a determination may be made as to whether the germicidal source is encased in the chamber at block 192 after the germicidal source and/or the shield has been moved to expose the germicidal source to an ambient of the apparatus in reference to the corrective action activated in block 194. In such cases, upon a determination that the germicidal source is not encased within a chamber, one or both of the process denoted in blocks 196 and 198 may be conducted.

Figure 16:
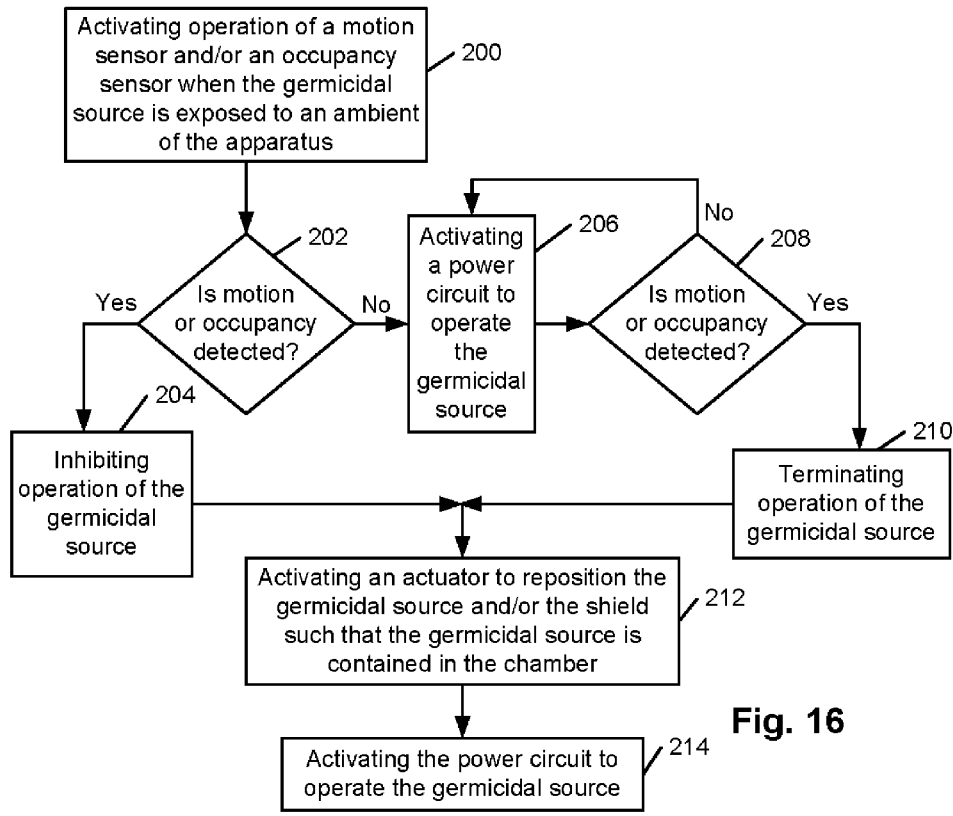
Figure 17:
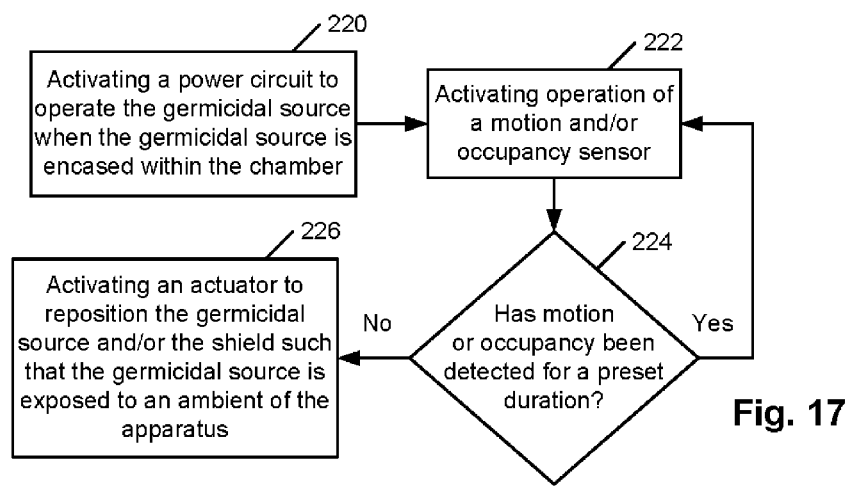

In some cases, an apparatus may switch between disinfection modes based on whether motion and/or occupancy is detected in a room or an area. FIGS. 16 and 17 illustrate flowcharts of processes facilitating such an objective. In particular, FIG. 16 shows block 200 in which a motion sensor and/or an occupancy sensor is activated to operate when the germicidal source extends outside of the apparatus. The activation may generally be conducted before the germicidal source is activated to operate. At block 202, a determination is made as to whether motion or occupancy is detected during a predetermined duration. As shown by block 204, if motion or occupancy is detected, operation of the germicidal source is inhibited. Conversely, if motion or occupancy is not detected during the predetermined amount of time, a power circuit of the apparatus is activated to operate the germicidal source as denoted in block 206.

Subsequent to commencing operation of the germicidal source, a determination is made at block 208 as to whether motion or occupancy is detected for a predetermined duration. If no motion or occupancy is detected during the predetermined amount of time, the power circuit continues to supply power to the germicidal source at block 206 for a room/area disinfection process and motion and/or occupancy continues to be monitored at block 208. In cases in which motion or occupancy is detected, operation of the germicidal source is terminated as denoted in block 210. Upon operation of the germicidal source being terminated in reference to block 210 or upon its operation being inhibited in reference to block 204, an actuator coupled to the germicidal source is activated and/or an actuator coupled to a shield of the apparatus is activated to reposition the coupled component/s such that the germicidal source is contained in a chamber of the apparatus as denoted in block 212. Subsequent thereto, the power circuit of the apparatus may be activated to operate the germicidal source as denoted in block 214 for a disinfection process conducted interior to the apparatus.

An alternative set of processes which may induce an apparatus to switch between disinfection modes based on whether motion and/or occupancy is detected in a room or an area is illustrated in FIG. 17. In particular, FIG. 17 shows block 220 in which power circuitry of a disinfection apparatus is activated to operate a germicidal source of the apparatus when the germicidal source is encased within the apparatus. Block 222 shows a motion sensor and/or an occupancy sensor is activated to operate subsequent to block 220, but it is noted that the order of blocks 220 and 222 may be reversed. In particular, the power circuitry of the apparatus may be activated to operate the germicidal source subsequent to the motion sensor and/or occupancy sensor being activated. In other embodiments, the germicidal source and the motion sensor and/or occupancy sensor may be activated to operate at the same time.

In any case, as denoted in block 224, a determination is made as to whether motion or occupancy has been detected for a predetermined duration. In cases when motion or occupancy has been detected, the power circuit continues to supply power to the germicidal source for an interior disinfection process for block 220 and motion and/or occupancy continues to be monitored for block 222. Upon not detecting movement and/or occupancy for the preset duration, an actuator coupled to the germicidal source is activated and/or an actuator coupled to a shield of the apparatus is activated to reposition the noted component/s such that the germicidal source is exposed to an ambient of the apparatus as denoted in block 226. In some cases, operation of the germicidal source may continue while the germicidal source and/or shield are moved. In yet other embodiments, operation of the germicidal source may be terminated upon not detecting movement and/or occupancy for the preset duration and then reactivated once the actuator/s have moved the appropriate component/s.

It will be appreciated to those skilled in the art having the benefit of this disclosure that this invention is believed to provide apparatuses used for disinfecting surfaces, objects and/or air interior to the apparatuses and exterior to the apparatuses. Further modifications and alternative embodiments of various aspects of the invention will be apparent to those skilled in the art in view of this description. For example, several configurations of apparatuses are described herein for achieving the noted objective, but the apparatuses considered herein are not necessarily limited to such configurations. Several other configurations may be considered for achieving the noted objective. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. The term "approximately" as used herein refers to variations of up to +/−5% of the stated number.

What is claimed is:

1. An apparatus, comprising:
   a germicidal source;
   power supply circuitry coupled to the germicidal source;
   a shield, wherein the shield and/or the germicidal source are moveable relative to each other, and wherein the apparatus is configured such that:
      the shield and/or the germicidal source may be brought in proximity to the other such that germicide projected from the germicidal source is substantially contained within an interior cavity of the apparatus; and
      the shield and/or the germicidal source may be brought out of proximity with the other such that germicide projected from the germicidal source is projected into an ambient of the apparatus;
   a sensor to detect whether the germicidal source and the shield are said in proximity with each other and/or to detect whether the germicidal source and the shield are said out of proximity with each other;
   an electronic user interface comprising input controls allowing selection of different disinfection modes conducted by the apparatus, wherein the different disinfection modes comprise a first disinfection mode for primarily disinfecting a medium inside the apparatus and a second disinfection mode for primarily disinfecting a medium exterior to the apparatus;
   a processor; and
   a storage medium having program instructions which are executable by the processor for:
      receiving input from the electronic user interface regarding a selected disinfection mode;
      upon receiving input of the first disinfection mode:
         determining whether the shield and the germicidal source are said in proximity with each other or said out of proximity with each other;
         upon determining the shield and the germicidal source are said out of proximity with each other, activating a corrective action for the germicidal source and/or the shield to be moved said in proximity with the other; and
         upon determining the shield and the germicidal source are said in proximity with each other, activating the power supply circuitry in accordance with a predetermined first set of operating parameters for the apparatus; and
      upon receiving input of the second disinfection mode:
         determining whether the shield and the germicidal source are said in proximity with each other or said out of proximity with each other;
         upon determining the shield and the germicidal source are said in proximity with each other, activating a corrective action for the germicidal source and/or the shield to be moved said out of proximity with the other; and
         upon determining the shield and the germicidal source are said out of proximity with each other, activating the power supply circuitry in accordance with a predetermined second set of operating parameters for the apparatus different from the first set of operating parameters, wherein the predetermined first and second sets of operating parameters comprise different amounts of power supplied from the power supply circuitry to operate the germicidal source.

2. The apparatus of claim 1, wherein the predetermined first set of operating parameters comprises a lower amount of power to operate the germicidal source than the predetermined second set of operating parameters.

3. The apparatus of claim 1, further comprising an air moving device to draw air into the interior cavity when the germicidal source and the shield are in proximity with each other.

4. The apparatus of claim 3, wherein the predetermined first and second sets of operating parameters comprise different speeds at which to operate the air moving device.

5. The apparatus of claim 4, wherein the predetermined first set of operating parameters comprises a higher speed to operate the air moving device than the predetermined second set of operating parameters.

6. The apparatus of claim 3, wherein the storage medium is void of program instructions for activating the air moving device upon receiving input of the second disinfection mode.

7. The apparatus of claim 1, wherein the germicidal source comprises:
   a germicidal lamp;
   a transparent barrier circumjacent the germicidal lamp forming a plenum around the germicidal lamp; and
   an air moving device to draw air into the plenum.

8. The apparatus of claim 1, further comprising:
   an additional sensor to detect movement and/or occupancy within an ambient of the apparatus; and
   an actuator coupled to the germicidal source or to the shield, wherein the program instructions for activating the corrective actions for the germicidal source and/or the shield to be moved comprise activating the actuator; and
   wherein the storage medium further comprises program instructions for:
      activating the additional sensor to operate upon receiving input of the first disinfection mode; and
      upon the additional sensor not detecting movement and/or occupancy for a preset duration, activating the actuator to move the germicidal source or the shield out of said proximity with the other.

9. The apparatus of claim 1, wherein the germicidal source is one of a plurality of germicidal sources of the apparatus coupled to the power supply circuitry, and wherein the storage medium comprises program instructions for:

activating the power supply circuitry to selectively operate a subset of the multiple germicidal sources upon receiving input of the first disinfection mode and upon determining the shield and the germicidal source are in proximity with each other; and activating the power supply circuitry to selectively operate a different subset of the multiple germicidal sources upon receiving input of the second disinfection mode and upon determining the shield and the germicidal source are not in proximity with each other.

10. The apparatus of claim 1, wherein the germicidal source is a germicidal lamp.

11. The apparatus of claim 1, wherein the germicidal source is a source of germicidal plasma, germicidal vapor, germicidal liquid, and/or germicidal gas.

12. The apparatus of claim 3, wherein the shield is a chamber, and wherein the chamber comprises:
a port dimensionally configured for the germicidal source to pass therethrough; and
a plenum extending between the port and the air moving device and/or an air inlet of the chamber.

13. The apparatus of claim 12, wherein the germicidal source is a germicidal lamp, and wherein the plenum comprises sidewalls that are transparent to germicidal light projected from the germicidal lamp.

14. The apparatus of claim 7, wherein the germicidal lamp is an ultraviolet lamp, and wherein the apparatus further comprises:
first and second air outlets to exhaust air from the plenum, wherein the first air outlet comprises an ozone reducing device; and
an air flow regulator arranged and configured to selectively allow air flow through the first air outlet and selectively allow air flow through the second air outlet, wherein the storage medium comprises program instructions for controlling the air flow regulator such that:
air is routed through the first air outlet when the power supply circuitry is activated in accordance with the predetermined first set of operating parameters; and
air is routed through the second air outlet when the power supply circuitry is activated in accordance with the predetermined second set of operating parameters.

15. The apparatus of claim 1, wherein the predetermined first and second sets of operating parameters comprise different durations for operating the germicidal source.

16. The apparatus of claim 1, wherein the germicidal source is a pulsed germicidal source, and wherein the predetermined first and second sets of operating parameters comprise different frequencies to pulse operation of the germicidal source.

17. The apparatus of claim 1, wherein the first disinfection mode comprises a first subset disinfection mode for primarily disinfecting air inside the interior cavity and a second subset disinfection mode for primarily disinfecting one or more objects inside the interior cavity.

18. The apparatus of claim 1, further comprising:
an additional sensor to detect movement and/or occupancy within an ambient of the apparatus; and
an actuator coupled to the germicidal source or to the shield, wherein the program instructions for activating the corrective actions for the germicidal source and/or the shield to be moved comprise activating the actuator; and
wherein the storage medium further comprises program instructions for:

activating the additional sensor to operate prior to activating the power supply circuitry in accordance with the predetermined second set of operating parameters;

inhibiting activation of the power supply circuitry upon the additional sensor detecting movement and/or occupancy prior to said activating the power supply circuitry in accordance with the predetermined second set of operating parameters;

terminating operation of the germicidal source upon the additional sensor detecting movement and/or occupancy subsequent to said activating the power supply circuitry in accordance with the predetermined second set of operating parameters;

upon said inhibiting activation of the power supply circuitry or terminating operation of the germicidal source, activating the actuator such that the shield and the germicidal source are said in proximity with each other; and subsequently activating the power supply circuitry to operate the germicidal source.

19. The apparatus of claim 1, wherein the shield is a chamber or is configured in accompaniment with features of the apparatus to form a chamber sufficient to encase the germicidal source within the interior cavity of the apparatus when the shield and the germicidal source are said in proximity with each other, and wherein the chamber comprises:
an input port accessing the interior cavity,
a door to open and close the input port; and
one or more shelves and/or baskets arranged along one or more interior walls of the chamber and/or along an interior portion of the door.

20. The apparatus of claim 1, wherein the shield comprises a heat shield and/or a heat sink.

21. The apparatus of claim 1, wherein the shield is a chamber or is configured in accompaniment with features of the apparatus to form a chamber sufficient to encase the germicidal source when the shield and the germicidal source are said in proximity with each other, and wherein the apparatus further comprises a cooling device and/or a dehumidifier within the chamber and/or in proximity to an air inlet of the chamber.

22. The apparatus of claim 1, further comprising a housing surrounding the germicidal source, wherein the shield is a chamber comprising a port that dimensionally configured to receive the germicidal source and the housing, and wherein the housing or the port comprises a seal.

23. The apparatus of claim 7, wherein the predetermined first and second sets of operating parameters comprise different speeds at which to operate the air moving device.

24. The apparatus of claim 23, wherein the predetermined first set of operating parameters comprises a higher speed to operate the air moving device than the predetermined second set of operating parameters.

25. The apparatus of claim 7, wherein the first disinfection mode comprises a first subset disinfection mode for primarily disinfecting air inside the plenum and a second subset disinfection mode for primarily disinfecting one or more objects inside the interior cavity.

26. An apparatus, comprising:
a germicidal source;
power supply circuitry coupled to the germicidal source;
a shield, wherein the shield and/or the germicidal source are moveable relative to each other, and wherein the apparatus is configured such that:

the shield and/or the germicidal source may be brought in proximity to the other such that germicide projected from the germicidal source is substantially contained within an interior cavity of the apparatus; and the shield and/or the germicidal source may be brought out of proximity with the other such that germicide projected from the germicidal source is projected into an ambient of the apparatus;

a sensor to detect whether the germicidal source and the shield are said in proximity with each other and/or to detect whether the germicidal source and the shield are said out of proximity with each other;

an electronic user interface comprising input controls allowing selection of different disinfection modes conducted by the apparatus, wherein the different disinfection modes comprise a first disinfection mode for primarily disinfecting a medium inside the apparatus and a second disinfection mode for primarily disinfecting a medium exterior to the apparatus;

an additional sensor to detect movement and/or occupancy within an ambient of the apparatus;

an actuator coupled to the germicidal source or to the shield;

a processor; and a storage medium having program instructions which are executable by the processor for:
receiving input from the electronic user interface regarding a selected disinfection mode;
upon receiving input of the first disinfection mode, determining whether the shield and the germicidal source are said in proximity with each other or said out of proximity with each other;
upon determining the shield and the germicidal source are said out of proximity with each other, activating the actuator to move the germicidal source and/or the shield said in proximity with the other;
upon determining the shield and the germicidal source are said in proximity with each other or subsequent to the actuator being activated to move the germicidal source and/or the shield said in proximity with the other:
activating the power supply circuitry in accordance with a predetermined first set of operating parameters for the apparatus;
activating the additional sensor; and
upon the additional sensor not detecting movement and/or occupancy for a preset duration, activating the actuator to move the germicidal source or the shield out of said proximity with the other; and
upon receiving input of the second disinfection mode, determining whether the shield and the germicidal source are said in proximity with each other or said out of proximity with each other;
upon determining the shield and the germicidal source are said in proximity with each other, activating the actuator to move the germicidal source and/or the shield said out of proximity with the other; and
upon determining the shield and the germicidal source are said out of proximity with each other or subsequent to the actuator being activated to move the germicidal source and/or the shield said out of proximity with the other, activating the power supply circuitry in accordance with a predetermined second set of operating parameters for the apparatus.

27. The apparatus of claim 26, wherein the storage medium further comprises program instructions for:
activating the additional sensor subsequent to receiving input of the second disinfection mode and prior to activating the power supply circuitry in accordance with the predetermined second set of operating parameters;
inhibiting activation of the power supply circuitry upon the additional sensor detecting movement and/or occupancy prior to said activating the power supply circuitry in accordance with the predetermined second set of operating parameters;
terminating operation of the germicidal source upon the additional sensor detecting movement and/or occupancy subsequent to said activating the power supply circuitry in accordance with the predetermined second set of operating parameters;
upon said inhibiting activation of the power supply circuitry or terminating operation of the germicidal source, activating the actuator such that the shield and the germicidal source are said in proximity with each other; and
subsequently activating the power supply circuitry to operate the germicidal source.

28. The apparatus of claim 26, wherein the predetermined first set of operating parameters are different from the second set of operating parameters.

29. An apparatus, comprising:
a germicidal source;
power supply circuitry coupled to the germicidal source;
a shield, wherein the shield and/or the germicidal source are moveable relative to each other, and wherein the apparatus is configured such that:
the shield and/or the germicidal source may be brought in proximity to the other such that germicide projected from the germicidal source is substantially contained within an interior cavity of the apparatus; and
the shield and/or the germicidal source may be brought out of proximity with the other such that germicide projected from the germicidal source is projected into an ambient of the apparatus;
a sensor to detect whether the germicidal source and the shield are said in proximity with each other and/or to detect whether the germicidal source and the shield are said out of proximity with each other;
an electronic user interface comprising input controls allowing selection of different disinfection modes conducted by the apparatus, wherein the different disinfection modes comprise:
a first disinfection mode for primarily disinfecting air inside the apparatus;
a second disinfection mode for primarily disinfecting objects inside the apparatus; and
a third disinfection mode for primarily disinfecting surfaces exterior to the apparatus;
a processor; and
a storage medium having program instructions which are executable by the processor for:
receiving input from the electronic user interface regarding a selected disinfection mode;
upon receiving input of the first disinfection mode or the second disinfection mode:

determining whether the shield and the germicidal source are said in proximity with each other or said out of proximity with each other;

upon determining the shield and the germicidal source are said out of proximity with each other, activating a corrective action for the germicidal source and/or the shield to be moved said in proximity with the other; and upon determining the shield and the germicidal source are said in proximity with each other:

activating the power supply circuitry in accordance with a predetermined first set of operating parameters for the apparatus if the received input is for the first disinfection mode;

activating the power supply circuitry in accordance with a predetermined second set of operating parameters for the apparatus if the received input is for the second disinfection mode, wherein the predetermined second set of operating parameters is different from the predetermined first set of operating parameters; and upon receiving input of the third disinfection mode:

determining whether the shield and the germicidal source are said in proximity with each other or said out of proximity with each other;

upon determining the shield and the germicidal source are said in proximity with each other, activating a corrective action for the germicidal source and/or the shield to be moved said out of proximity with the other; and upon determining the shield and the germicidal source are said out of proximity with each other, activating the power supply circuitry in accordance with a predetermined third set of operating parameters, wherein the predetermined third set of operating parameters is different from the predetermined first and second sets of operating parameters.

30. The apparatus of claim 29, wherein the predetermined first, second and third sets of operating parameters comprise different amounts of power supplied from the power supply circuitry to operate the germicidal source.

31. The apparatus of claim 29, further comprising an air moving device to draw air into the interior cavity when the germicidal source and the shield are in proximity with each other, wherein the predetermined first, second and third sets of operating parameters comprise different speeds at which to operate the air moving device.

32. The apparatus of claim 29, wherein the predetermined first, second and third sets of operating parameters comprise different durations for operating the germicidal source.

33. The apparatus of claim 29, wherein the germicidal source is a pulsed germicidal source, and wherein the predetermined first, second and third sets of operating parameters comprise different frequencies to pulse operation of the germicidal source.

34. The apparatus of claim 29, wherein the shield comprises one or more shelves and/or baskets.

* * * * *

UNITED STATES PATENT AND TRADEMARK OFFICE
CERTIFICATE OF CORRECTION

PATENT NO. : 9,867,894 B2  
APPLICATION NO. : 14/790827  
DATED : January 16, 2018  
INVENTOR(S) : Stibich et al.

Page 1 of 1

It is certified that error appears in the above-identified patent and that said Letters Patent is hereby corrected as shown below:

In Claim 22, Column 38, Line 47, insert --is-- after "that"

Signed and Sealed this
Sixteenth Day of October, 2018

Andrei Iancu
*Director of the United States Patent and Trademark Office*